(12) United States Patent
Beyer et al.

(10) Patent No.: US 12,106,650 B2
(45) Date of Patent: Oct. 1, 2024

(54) PSAP/PUBLIC RESPONDER NETWORK INTEGRATIONS

(71) Applicant: Avive Solutions, Inc., Brisbane, CA (US)

(72) Inventors: Rory M. Beyer, San Mateo, CA (US); Sameer Jafri, San Diego, CA (US); Gordon Moseley P. Andrews, Ross, CA (US)

(73) Assignee: Avive Solutions, Inc., Brisbane, CA (US)

(*) Notice: Subject to any disclaimer, the term of this patent is extended or adjusted under 35 U.S.C. 154(b) by 197 days.

(21) Appl. No.: 17/903,642

(22) Filed: Sep. 6, 2022

(65) Prior Publication Data

US 2023/0008570 A1    Jan. 12, 2023

Related U.S. Application Data

(63) Continuation-in-part of application No. 17/471,572, filed on Sep. 10, 2021, now Pat. No. 11,645,899, which is a continuation-in-part of application No. 16/863,068, filed on Apr. 30, 2020, now Pat. No. 11,138,855, which is a continuation-in-part of application No. 16/741,277, filed on Jan. 13, 2020, now Pat. No. 10,665,078, which is a continuation of
(Continued)

(51) Int. Cl.
| | |
|---|---|
| *G08B 21/02* | (2006.01) |
| *G08B 25/00* | (2006.01) |
| *G08B 25/14* | (2006.01) |
| *G08B 27/00* | (2006.01) |
| *H04W 4/16* | (2009.01) |
| *H04W 4/90* | (2018.01) |
| *A61N 1/39* | (2006.01) |
| *H04W 4/02* | (2018.01) |

(52) U.S. Cl.
CPC .......... *G08B 21/02* (2013.01); *G08B 25/006* (2013.01); *G08B 25/14* (2013.01); *G08B 27/001* (2013.01); *H04W 4/16* (2013.01); *H04W 4/90* (2018.02); *A61N 1/3904* (2017.08); *H04W 4/02* (2013.01)

(58) Field of Classification Search
CPC ....................................................... G08B 21/02
See application file for complete search history.

(56) References Cited

U.S. PATENT DOCUMENTS

| | | |
|---|---|---|
| 6,292,687 B1 | 9/2001 | Lowell et al. |
| 6,356,785 B1 | 3/2002 | Snyder et al. |
| | (Continued) | |

FOREIGN PATENT DOCUMENTS

| | | |
|---|---|---|
| CN | 105013085 | 11/2015 |
| CN | 108671401 | 10/2019 |
| | (Continued) | |

*Primary Examiner* — Travis R Hunnings
(74) *Attorney, Agent, or Firm* — Beyer Law Group LLP

(57) ABSTRACT

A variety of dispatcher user interfaces, communications architectures, methods, apparatus, APIs and protocols are described that can help facilitate the integration of volunteer responder networks into the workflows of PSAP dispatchers. In one aspect, a dispatcher user interface facilitates activation of the volunteer responder network, as well as tracking and/or communicating notes to medical devices such as AEDs in the responder network that have accepted an incident.

24 Claims, 13 Drawing Sheets

Related U.S. Application Data application No. 16/562,870, filed on Sep. 6, 2019, now Pat. No. 10,580,280.

(60) Provisional application No. 63/242,610, filed on Sep. 10, 2021, provisional application No. 62/846,346, filed on May 10, 2019, provisional application No. 62/731,306, filed on Sep. 14, 2018.

(56) References Cited

U.S. PATENT DOCUMENTS

| | | | |
|---|---|---|---|
| 6,493,581 B2 | 12/2002 | Russell | |
| 6,658,290 B1 | 12/2003 | Lin et al. | |
| 6,747,556 B2 | 6/2004 | Medema et al. | |
| 6,834,207 B2 | 12/2004 | Miyauchi et al. | |
| 6,937,150 B2 | 8/2005 | Medema et al. | |
| 6,993,386 B2 | 1/2006 | Lin et al. | |
| 7,289,029 B2 | 10/2007 | Medema et al. | |
| 8,086,320 B2 | 12/2011 | Saketkhou | |
| 8,180,457 B2 | 5/2012 | Matos | |
| 8,209,008 B2 | 6/2012 | Hansen et al. | |
| 8,565,871 B2 | 10/2013 | Tuysserkani | |
| 8,706,225 B2 | 4/2014 | Matos | |
| 8,818,522 B2 | 8/2014 | Mass et al. | |
| 8,880,168 B2 | 11/2014 | Pearce et al. | |
| 8,981,927 B2 | 3/2015 | McSheffrey | |
| 9,026,147 B2 | 5/2015 | Galvin et al. | |
| 9,035,787 B2 | 5/2015 | Bongberg et al. | |
| 9,101,527 B2 | 8/2015 | Madanat | |
| 9,232,040 B2 | 1/2016 | Barash et al. | |
| 9,289,621 B2 | 3/2016 | Aoyama et al. | |
| 9,295,849 B2 | 3/2016 | Elghazzawi et al. | |
| 9,307,383 B1 | 4/2016 | Patrick | |
| 9,324,120 B2 | 4/2016 | Braun | |
| 9,480,852 B2 | 11/2016 | Bonnamy | |
| 9,498,152 B2 | 11/2016 | Bowers | |
| 9,592,401 B2 | 3/2017 | Freeman et al. | |
| 9,619,767 B2 | 4/2017 | Braun | |
| 9,628,946 B2 | 4/2017 | Elghazzawi | |
| 9,847,030 B2 | 12/2017 | Kadobayashi et al. | |
| 9,848,058 B2 | 12/2017 | Johnson et al. | |
| 9,872,998 B2 | 1/2018 | Aoyama et al. | |
| 9,889,311 B2 | 2/2018 | Horseman et al. | |
| 9,897,459 B2 | 2/2018 | Johnson | |
| 9,987,193 B2 | 5/2018 | Freeman | |
| 10,035,023 B2 | 7/2018 | Das | |
| 10,058,469 B2 | 8/2018 | Freeman | |
| 10,058,709 B2 | 8/2018 | Tilton, Jr. | |
| 10,090,716 B2 | 10/2018 | Stever et al. | |
| 10,092,767 B1 | 10/2018 | Newton et al. | |
| 10,099,061 B2 | 10/2018 | Buchanan | |
| 10,159,848 B2 | 12/2018 | Amann et al. | |
| 10,178,534 B2 | 1/2019 | Barash et al. | |
| 10,298,072 B2 | 5/2019 | Stever et al. | |
| 10,381,118 B2 | 8/2019 | Kellum | |
| 10,449,380 B2 | 10/2019 | Andrews | |
| 10,504,622 B2 | 12/2019 | Gallopyn et al. | |
| 10,543,379 B2 | 1/2020 | Hingston et al. | |
| 10,565,845 B1 * | 2/2020 | Beyer | G08B 21/02 |
| 10,580,280 B1 | 3/2020 | Picco et al. | |
| 10,621,846 B1 | 4/2020 | Beyer et al. | |
| 10,638,929 B2 | 5/2020 | Kaib et al. | |
| 10,657,796 B2 | 5/2020 | Bowers | |
| 10,665,078 B1 | 5/2020 | Picco et al. | |
| 10,744,063 B2 | 8/2020 | Freeman | |
| 10,773,091 B2 | 9/2020 | Andrews et al. | |
| 10,792,506 B2 | 10/2020 | Elghazzawi | |
| 10,796,396 B2 | 10/2020 | Braun et al. | |
| 10,806,939 B1 | 10/2020 | Malott et al. | |
| 10,857,371 B2 | 12/2020 | Gustavson et al. | |
| 10,861,310 B2 | 12/2020 | Picco et al. | |
| 10,946,209 B2 | 3/2021 | Andrews et al. | |
| 10,957,178 B2 | 3/2021 | Beyer et al. | |
| 11,077,312 B2 | 8/2021 | Sturman et al. | |
| 11,138,855 B2 | 10/2021 | Jafri et al. | |
| 2003/0149759 A1 | 8/2003 | Hetherington et al. | |
| 2004/0015191 A1 | 1/2004 | Otman et al. | |
| 2004/0049233 A1 | 3/2004 | Edwards | |
| 2004/0064342 A1 | 4/2004 | Browne et al. | |
| 2006/0030891 A1 | 2/2006 | Saltzstein et al. | |
| 2006/0041278 A1 | 2/2006 | Cohen et al. | |
| 2006/0149321 A1 | 7/2006 | Merry et al. | |
| 2006/0149322 A1 | 7/2006 | Merry et al. | |
| 2006/0149323 A1 | 7/2006 | Merry et al. | |
| 2007/0032830 A1 | 2/2007 | Bowers | |
| 2007/0136099 A1 | 6/2007 | Neligh et al. | |
| 2007/0162075 A1 | 7/2007 | O'hara | |
| 2007/0270909 A1 | 11/2007 | Saketkhou | |
| 2007/0299473 A1 * | 12/2007 | Matos | A61N 1/3904 607/9 |
| 2008/0250166 A1 | 10/2008 | Edwards | |
| 2009/0070148 A1 | 3/2009 | Skocic | |
| 2009/0149894 A1 | 6/2009 | Merry et al. | |
| 2009/0284348 A1 * | 11/2009 | Pfeffer | G08B 25/006 340/7.3 |
| 2009/0284378 A1 * | 11/2009 | Ferren | G08B 21/06 340/573.1 |
| 2010/0017471 A1 | 1/2010 | Brown et al. | |
| 2010/0286490 A1 * | 11/2010 | Koverzin | G08B 21/0492 704/231 |
| 2011/0060378 A1 | 3/2011 | Tuysserkani | |
| 2011/0071880 A1 * | 3/2011 | Spector | H04W 76/50 340/539.13 |
| 2011/0117878 A1 | 5/2011 | Barash et al. | |
| 2011/0152702 A1 * | 6/2011 | Goto | G08B 21/02 340/7.58 |
| 2012/0232355 A1 | 9/2012 | Freeman | |
| 2012/0271370 A1 | 10/2012 | Hochhalter et al. | |
| 2013/0012151 A1 | 1/2013 | Hankins | |
| 2013/0065628 A1 | 3/2013 | Pfeffer | |
| 2013/0296719 A1 | 11/2013 | Packer et al. | |
| 2014/0002241 A1 | 1/2014 | Elghazzawi | |
| 2014/0004814 A1 | 1/2014 | Elghazzawi | |
| 2014/0031884 A1 | 1/2014 | Elghazzawi | |
| 2014/0222096 A1 | 8/2014 | Hu et al. | |
| 2014/0222466 A1 | 8/2014 | Kellum | |
| 2015/0206408 A1 * | 7/2015 | LaLonde | A61B 5/0026 340/539.12 |
| 2015/0343229 A1 * | 12/2015 | Peterson | G16Z 99/00 607/6 |
| 2016/0066653 A1 | 3/2016 | Piva et al. | |
| 2016/0133160 A1 | 5/2016 | Packer et al. | |
| 2016/0140834 A1 * | 5/2016 | Tran | G08B 25/016 340/539.11 |
| 2016/0148495 A1 | 5/2016 | Buchanan | |
| 2016/0210581 A1 | 7/2016 | Braun | |
| 2016/0213942 A1 | 7/2016 | Elghazzawi et al. | |
| 2016/0217691 A1 * | 7/2016 | Kadobayashi | G16H 40/20 |
| 2016/0328950 A1 | 11/2016 | Pelletier et al. | |
| 2017/0028211 A1 | 2/2017 | Tilton, Jr. | |
| 2017/0172424 A1 | 6/2017 | Eggers et al. | |
| 2017/0251347 A1 | 8/2017 | Mehta et al. | |
| 2017/0281016 A1 | 10/2017 | Elghazzawi | |
| 2017/0281461 A1 | 10/2017 | Kokubo et al. | |
| 2017/0289350 A1 | 10/2017 | Philbin | |
| 2017/0367927 A1 | 12/2017 | Cervantes | |
| 2018/0169426 A1 | 6/2018 | Montague et al. | |
| 2018/0369598 A1 | 12/2018 | Newton et al. | |
| 2019/0038133 A1 | 2/2019 | Tran | |
| 2019/0044362 A1 | 2/2019 | Beyer et al. | |
| 2019/0099608 A1 | 4/2019 | Elghazzawi et al. | |
| 2019/0117983 A1 | 4/2019 | Andrews et al. | |
| 2019/0117984 A1 | 4/2019 | Andrews et al. | |
| 2019/0117987 A1 | 4/2019 | Beyer et al. | |
| 2019/0117988 A1 | 4/2019 | Beyer et al. | |
| 2019/0159009 A1 | 5/2019 | Barash et al. | |
| 2019/0168010 A1 | 6/2019 | Elghazzawi | |
| 2019/0174289 A1 | 6/2019 | Martin et al. | |
| 2019/0279327 A1 | 9/2019 | Braun et al. | |
| 2019/0306664 A1 | 10/2019 | Mehta et al. | |
| 2019/0318827 A1 | 10/2019 | Chiu et al. | |
| 2020/0054885 A1 | 2/2020 | Aprile | |
| 2020/0090483 A1 | 3/2020 | Picco et al. | |

(56) References Cited

U.S. PATENT DOCUMENTS

| | | | |
|---|---|---|---|
| 2020/0092700 A1 | 3/2020 | Picco et al. | |
| 2020/0206517 A1* | 7/2020 | Martin et al. | |
| 2020/0221263 A1* | 7/2020 | Sturman | G16H 40/63 |
| 2020/0242907 A1 | 7/2020 | Beyer et al. | |
| 2020/0286352 A1* | 9/2020 | Beyer | G08B 27/005 |
| 2020/0286353 A1* | 9/2020 | Jafri | G08B 21/02 |
| 2020/0373005 A1 | 11/2020 | Halsne et al. | |
| 2021/0142639 A1* | 5/2021 | Beyer | G08B 25/14 |
| 2021/0153817 A1 | 5/2021 | Beyer et al. | |
| 2021/0154487 A1 | 5/2021 | Bongberg et al. | |
| 2021/0228893 A1* | 7/2021 | Akram | A61N 1/3925 |
| 2021/0357456 A1* | 11/2021 | Hale | G01W 1/10 |
| 2021/0407273 A1 | 12/2021 | Jafri et al. | |
| 2022/0092957 A1* | 3/2022 | Beyer | H04W 4/023 |
| 2022/0093957 A1 | 3/2022 | Beyer et al. | |

FOREIGN PATENT DOCUMENTS

| | | |
|---|---|---|
| CN | 111539866 | 8/2020 |
| DE | 202004002106 | 6/2004 |
| EP | 1157717 | 1/2005 |
| EP | 2218478 | 8/2010 |
| EP | 2879759 | 10/2019 |
| JP | 2001/325689 | 11/2001 |
| JP | 2015-58030 | 3/2015 |
| KR | 20160012239 | 2/2016 |
| KR | 101780214 | 10/2017 |
| KR | 102152282 | 9/2020 |
| WO | 2010/66014 | 6/2010 |
| WO | 2018/069383 | 4/2018 |

\* cited by examiner

PSAP/PUBLIC RESPONDER NETWORK INTEGRATIONS

CROSS-REFERENCE TO RELATED APPLICATIONS

This application claims priority of U.S. Provisional Application No. 63/242,610, filed Sep. 10, 2021. Additionally, this application is a Continuation-in-Part of application Ser. No. 17/471,572, filed Sep. 10, 2021, which is a Continuation-in-Part of U.S. application Ser. No. 16/863,068, filed on Apr. 30, 2020 (now U.S. Pat. No. 11,138,855 issued on Oct. 5, 2021) which is a Continuation-in-Part of U.S. application Ser. No. 16/741,277, filed on Jan. 13, 2020 (now U.S. Pat. No. 10,665,078, issued on May 26, 2020), which is a Continuation of U.S. application Ser. No. 16/562,870, filed on Sep. 6, 2019 (now U.S. Pat. No. 10,580,280, issued Mar. 3, 2020), which claims the priority of U.S. Provisional Patent Application Nos. 62/731,306 filed Sep. 14, 2018, and 62/846,346 filed May 10, 2019. Each of foregoing patents and patent applications are incorporated herein by reference in their entirety.

FIELD

The present disclosure relates generally to the integration of emergency call centers (e.g., public-safety answering points (PSAPs)) with public responder networks. Many of the inventions described herein are particularly applicable to public responder networks suitable for responding to cardiac arrests.

BACKGROUND

Sudden cardiac arrest is one of the leading causes of death. In the United States alone, roughly 350,000 people die each year from sudden cardiac arrest. It is the leading cause of death for individuals over 40 and the #1 killer of student athletes. The most effective treatment for sudden cardiac arrest is the use of CPR coupled with defibrillation. Automated external defibrillators (AEDs) are portable devices designed to automatically check for life-threatening heart rhythms associated with sudden cardiac arrest and to send an electrical shock to the heart to try to restore a normal rhythm when shockable heart rhythms are detected. The two most common conditions treated by AEDs are Pulseless Ventricular tachycardia (aka VT or V-Tach) and Ventricular fibrillation (VF or V-Fib). AEDs are typically designed so that they can be used by a lay person in situations where professional medical help is not available.

Given their potential to save lives, automated external defibrillators have been deployed in a relatively wide variety of public and private locations so that they are available in the event that a person in the vicinity goes into cardiac arrest. By way of example, AEDs may be found in corporate and government offices, shopping centers, airports, airplanes, restaurants, casinos, hotels, sports stadiums, schools, fitness centers and a variety of other locations where people may congregate.

Applicant's U.S. Pat. No. 10,580,280 (P014B) and U.S. Pat. No. 10,665,078 (P014BC1), which are incorporated herein by reference, and others describe arrangements for integrating AED inclusive public responder networks with public-safety answering points (PSAPs). The present application describes additional features which further enhance such integrations.

SUMMARY

A variety of dispatcher user interfaces, communications architectures, methods, apparatus, APIs and protocols are described that facilitate the integration of AED responder networks into the workflows of PSAP dispatchers.

In one aspect, a dispatcher user interface suitable for display on a dispatcher display screen at a public-safety answering point is provided to facilitate tracking volunteer responder network AEDs that have accepted an incident. In some embodiments, the dispatcher user interface includes a GUI widget that a dispatcher can utilize to activate a responder network that includes one or more automated external defibrillators (AEDs). The user interface is further configured to display a map of a region that includes a location of the emergency incident and to also display one or more accepting AED icons on the map that each show the location of an associated AED that has accepted the incident. The placement of the accepting AED icon(s) on the map are periodically updated to show updated locations of the corresponding AED(s). In this manner, the dispatcher may track the location of the accepting AED(s) as they are transported to the location of an emergency incident. The location of the accepting AED icons are preferably updated on a regular basis, as for example, at least once every 15 seconds or less so that the dispatcher has a good understanding of the current location of the accepting AEDs.

In some embodiments, the user interface is further configured to alter the appearance of an accepting AED icon when the corresponding AED arrives at the location of the emergency incident. In some embodiments, such an appearance change may be triggered by the reception of an Arrived message sent in response to an arrived input made by a responder on an associated AED.

In some embodiments, an AED is deemed to have accepted an incident when the dispatcher user interface receives a notification triggered by a responder making an acceptance input to the corresponding AED.

In another aspect, a dispatcher user interface is configured to display a set of AED icons on a map that each correspond to an AED that is in the vicinity of an emergency incident. AED icons representing AEDs that have accepted an incident are rendered with a different visual appearance than AEDs that have not accepted the incident. The different visual appearance may take a variety of different forms, as for example, different colors, different sizes, different shapes, different images, etc. In some preferred embodiments, the dispatcher user interface is further configured to periodically update the placement of the accepting AED icons to show updated current locations of the corresponding AED as the corresponding AED is transported to the location of the emergency incident.

In some embodiments the dispatcher user interface is further configured to display one or more volunteer responder icons on the map that each represent the location of a volunteer responder that has accepted the emergency incident. Preferably the volunteer responder icons have a different visual appearance than AED icons. In some embodiments volunteer responders are not marked on the map before they have accepted an incident.

In some embodiments, the responder network is configured to notify volunteer responders of nearby incidents by a variety of different paths including notifying at least a first set of volunteer responders via mobile communication devices and a second set of volunteer responders via smart speakers.

In another aspect a dispatcher user interface includes a GUI widget suitable for use by a dispatcher to: (i) at least one of input, select or confirm a location of the emergency incident; (ii) input dispatcher notes; and (iii) cause a responder network activation message to be sent that directly or indirectly causes one or more medical devices that are in a vicinity of the emergency incident to generate a nearby incident alert configured to inform bystanders that there is a potential medical incident nearby for which the medical device may be helpful. In some embodiments, the medical devices are automated external defibrillators.

In some embodiments, the responder network activation message includes geographic coordinates of the location of the emergency incident. In some embodiments, the responder network activation alert includes the dispatcher notes inputted by a dispatcher.

In some embodiments, the responder network activation message is sent directly or indirectly to a responder network server that identifies the one or more medical devices and sends nearby incident messages to the one or more medical devices thereby causing the one or more medical devices to generate the nearby incident alert(s).

Corresponding methods of activating responder networks and managing responses are also described.

BRIEF DESCRIPTION OF THE DRAWINGS

The invention and the advantages thereof, may best be understood by reference to the following description taken in conjunction with the accompanying drawings in which.

In the drawings, like reference numerals are sometimes used to designate like structural elements. It should also be appreciated that the depictions in the figures are diagrammatic and not to scale.

DETAILED DESCRIPTION

The present disclosure relates generally to the integration of public-safety answering points (PSAPs) with public responder networks—as for example, a network of defibrillators (e.g. AEDs) available for use during a potential cardiac arrest incident and/or a network of volunteer responders willing to respond to such an event. A variety of methods, devices, user interfaces and software applications are described that enable dispatchers to activate public responder networks and/or support bystanders and/or volunteer responders during emergency incidents. The inventions are described primarily in the context of a network of defibrillators and volunteers willing to respond to cardiac arrest incidents. However, it should be appreciated that similar approaches and systems can be used in conjunction with responder networks involving other types of incidents, treatments and/or devices.

The Applicant is developing automated external defibrillator systems that include a number of connectivity features and/or are well suited for use in AED inclusive public responder networks. By way of example, U.S. Pat. No. 10,773,091 (P006E); U.S. Pat. No. 10,737,105 (P006A); U.S. Pat. No. 11,077,312 (P016B), and U.S. Pat. No. 10,029,109 (P001A) (each of which is incorporated herein by reference) describe a few such devices.

Figure 1A:
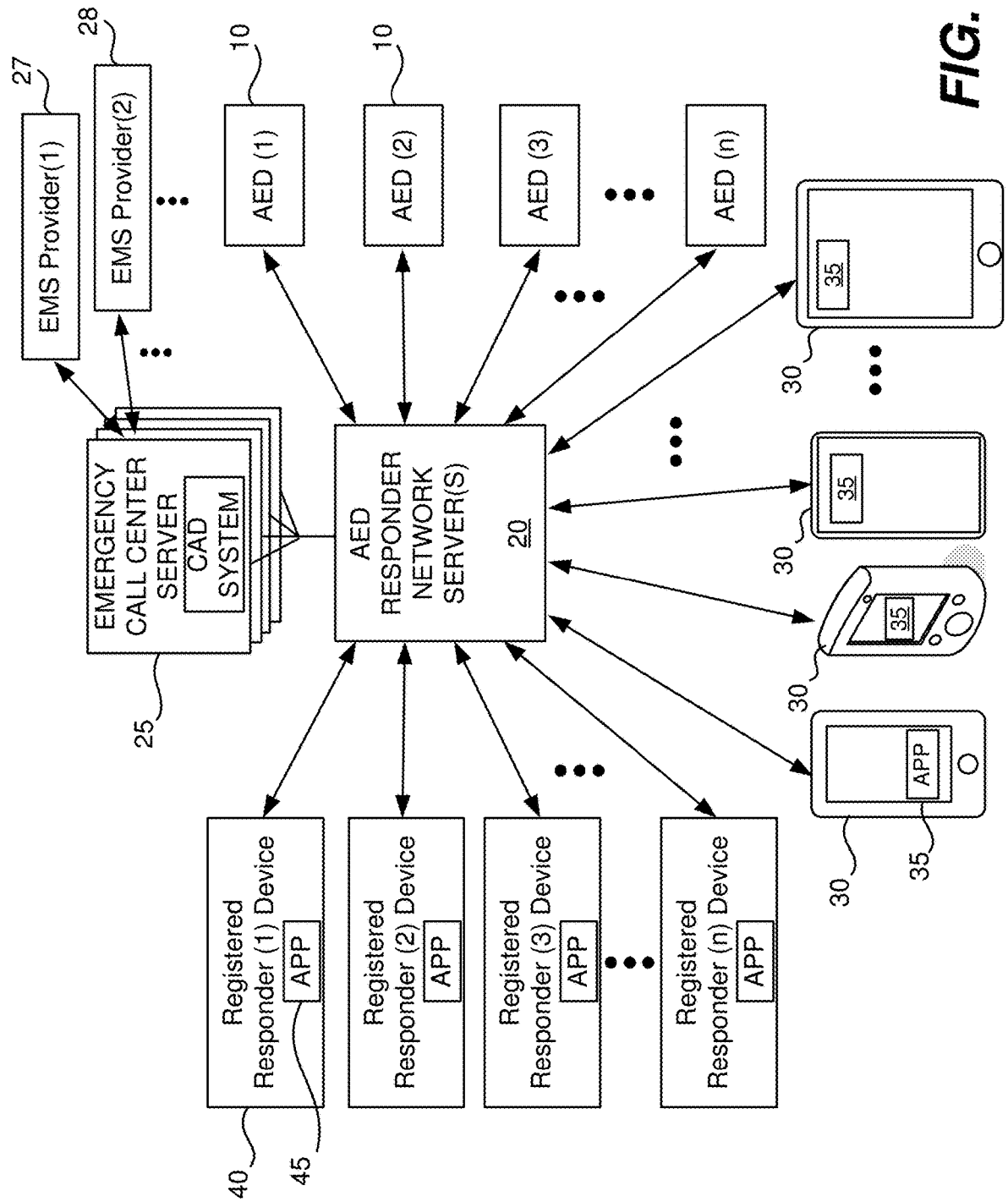
FIG. 1A is a schematic diagram illustrating components of a public responder network for notifying potential responders of nearby potential cardiac arrest incidents.
Figure 1B:
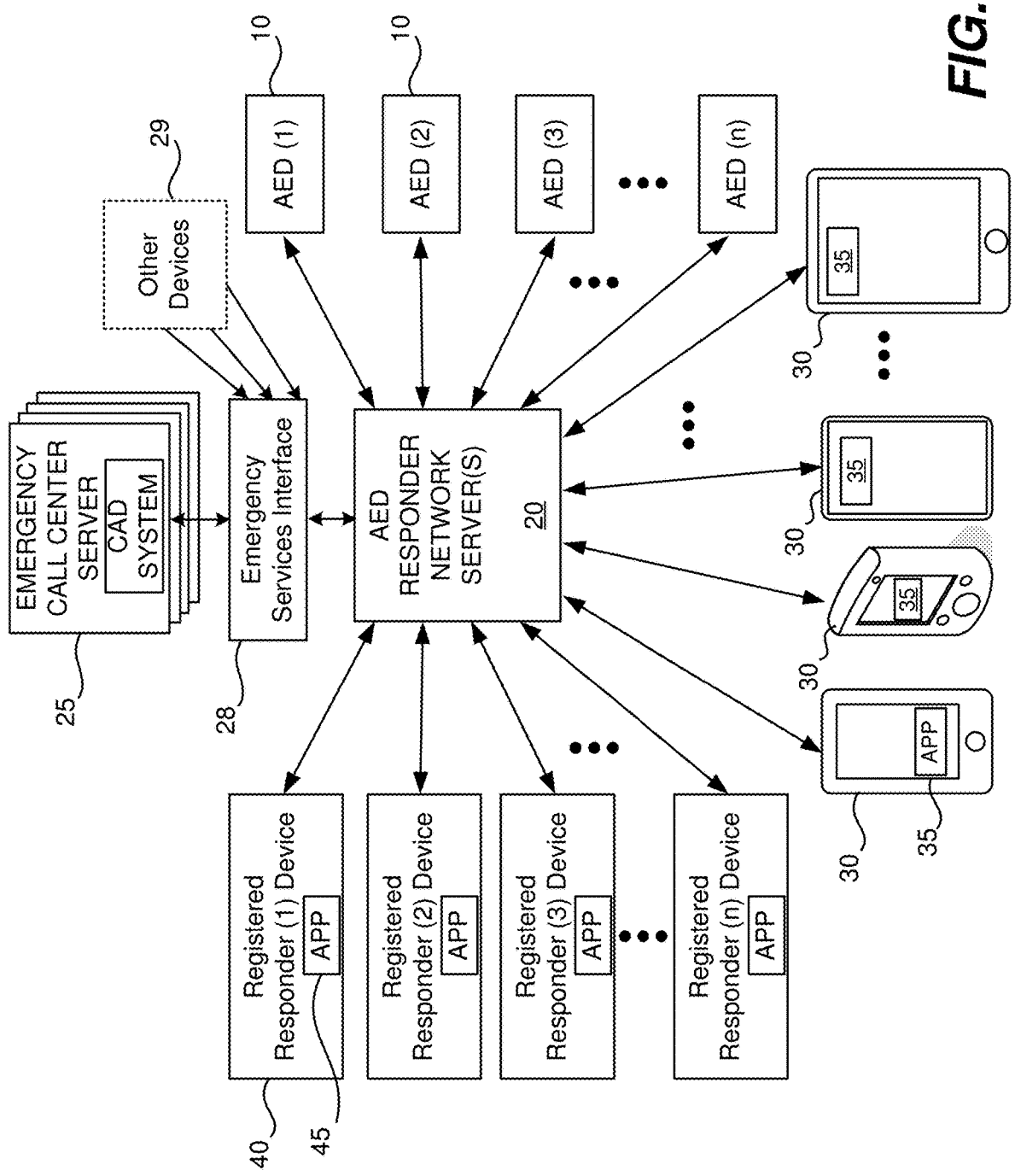
FIG. 1B is a schematic diagram illustrating components of an alternative public responder network for notifying potential responders of nearby potential cardiac arrest incidents that utilizes an emergency services interface.

Components of a public, AED inclusive responder network of the type contemplated herein are diagrammatically illustrated in FIGS. 1A and 1B. In the embodiment illustrated in FIG. 1A, the network includes a number of AEDs 10 that have connectivity features which facilitate communications with one or more servers—which is/are referred to in FIG. 1A as AED response network server(s) 20. Some of the AEDs described in the incorporated patents and patent applications work well for this purpose, but the network is not in any way limited to such AED. In some embodiments, some of the AEDs 10 may be modular defibrillator systems that include a fully functional base defibrillator and an interface unit that is mounted on and detachably attached to the base defibrillator unit to provide a unitary portable modular defibrillator. In such embodiments, the interface unit may include components such as a display screen and a communication unit suitable for communicating with the AED response network server through an appropriate communications network. The incorporated U.S. Pat. No. 10,773,091 (P006E); U.S. Pat. No. 10,737,105 (P006A); and U.S. Pat. No. 11,077,312 (P016B) describe some such systems. In other embodiments, the communications capabilities may be provided in a variety of different ways. For example, the communications module may be incorporated into a unitary defibrillator housing, or in a modular system, into the base defibrillator unit. Alternatively, the communications unit may be a unit that plugs into a defibrillator or takes any other suitable form.

The AED response network server(s) 20 is arranged to communicate directly or indirectly with existing emergency response networks and systems, including, for example, computer aided dispatch (CAD) systems commonly used by emergency call/dispatch centers. These are sometimes collectively referred to as emergency services servers (25) and a particular class of emergency services servers referred to as emergency call center servers(s) is illustrated in FIG. 1A. Emergency call centers are Public Safety Answering Points (PSAPs) such as 911 call centers in the U.S. and Canada, 112 call centers in Europe, 999 call centers in some jurisdictions and other such emergency services call centers.

The emergency call/dispatch centers 25 are typically able to communicate separately with a variety of emergency medical service providers (EMS providers) 27 which may include emergency medical technicians, ambulance services, fire department personnel, etc.

In various embodiments, the AED response network server can be hosted by an advocacy group or a private party such as a defibrillator manufacturer or an entity that manages a large number of AEDs. Alternatively, the functionality of AED response network server(s) 20 could be incorporated into a server (or servers) within an emergency services interface (discussed below). In other embodiments, the functionality of the AED response server(s) 20 can be incorporated into other components of public safety and/or emergency response networks.

The network may also include a number of user devices 30 each having a user app 35 or other suitable software installed thereon that is configured to communicate with one or more of the AEDs, and with the AED response network server 20. The AED user devices 30 are frequently (but not necessarily) devices associated with the AED's owners, administrators and/or other responsible parties. The AED user devices 30 may take a wide variety of different forms including mobile phones, tablet computers, as well as other types of personal communication and/or computing devices. The network also has a number of volunteer responders who have registered to indicate their desire to receive notification of nearby emergency incidents for which assistance may be helpful. In the context of a responder network focused on sudden cardiac arrest, the responders would presumably and preferably be trained in CPR and the use of an AED.

The volunteer responders have their own user devices 40 (e.g. smart phones, tablets, smart watches, or other computing or mobile/personal communication devices) which have a responder app 45 or other suitable software installed thereon with which they can communicate and receive communications from the AED response network server 20. Like the AED user devices 30 and user app 35, the responder user devices 40 and responder app 45 may take a wide variety of different forms (e.g. smart phones, tablets, smart watches or other computing or mobile/personal communication devices) and they are labeled differently in the drawings merely to highlight the different context that the devices and app are used for. In some embodiments, a single app may be used as both apps 35 and 45 with the primary difference being whether the user has registered as a volunteer responder or as an AED administrator/owner, and the functionality of the app that may be accessed after such registration. Of course, in other embodiments separate apps may be provided. It should be appreciated that there is no need for all of the apps to be the same and/or to come from one source. Rather, the emergency response functionality can be incorporated into a wide variety of different applications or software components provided by different entities, including different defibrillator manufacturers, different health service providers, different advocacy groups, different emergency service providers, different user device manufacturers, etc.

In some specific implementations, the user app may be embodied in the form of an AED app that is designed to be capable of use in conjunction with selected defibrillators during the event of an emergency to help guide a lay responder through the use of the AED and/or to help facilitate the transmission of incident information to emergency responders and other concerned medical personnel. Thus, for convenience, in much of the discussion below, the app is referred to as an AED app. However, it should be appreciated that the user application software may take a very wide variety of forms and is not intended to be limited to apps having AED support functionalities.

The AED response network server(s) 20 can also take a wide variety of different forms and are generally intended to refer to any central systems or combinations of systems configured to execute the necessary functionality of the server. By way of example the AED response network server may take the form of one or more computing devices, server clusters, distributed computing nodes on a network or the combined forces of multiple distinct systems. Such servers can be operated by public or private entities of any nature including emergency services, non-profit advocacy organizations, healthcare organizations, medical device companies, government agencies and/or any other suitable entities. The AED response network servers can be dedicated to handling AED response network actions, they can be integrated into AED management server platforms, they can be integrated into components of existing emergency services networks, and/or they can be deployed as part of a variety of other now existing or later developed systems.

FIG. 1B illustrates another representative responder network architecture. This embodiment is quite similar to the embodiment discussed above with respect to FIG. 1A except that an emergency response network interface or an emergency services interface 28 serves as an interface between the AED response network server 20 and the emergency call centers 25. In the United States, RapidSOS and RapidDeploy are currently a couple of the largest emergency response network interface and are well suited for such applications. One particularly desirable feature of existing emergency response network interfaces is that they currently have relationships with a large percentage of the emergency call centers in the United States and are already set up to send incident related data received from other connected devices 29 to various call centers—although they do not currently serve as an intermediary between call centers and any defibrillators or defibrillator networks. Although RapidSOS is mentioned specifically, it should be appreciated that the same approach can be used with any or with multiple different intermediaries as appropriate.

Figure 2:
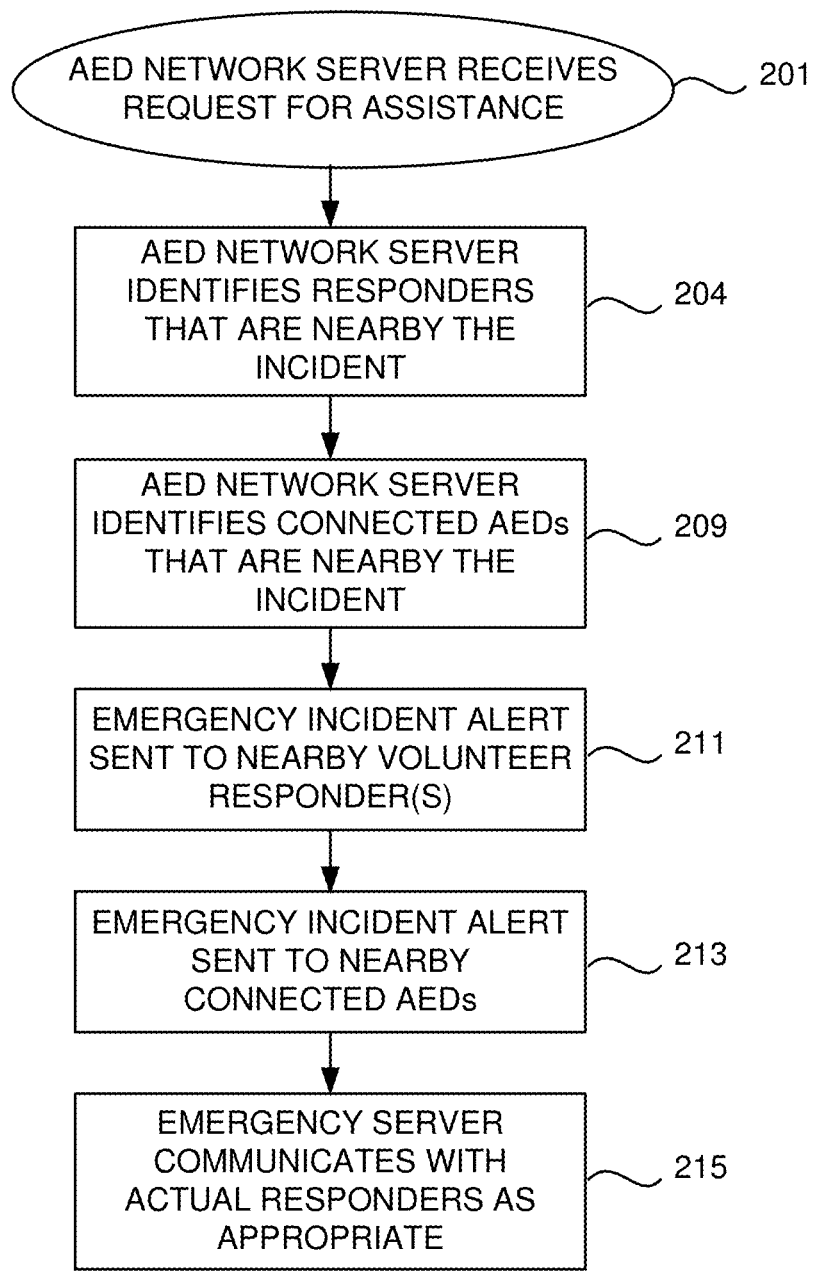
FIG. 2 is a flow chart illustrating a flow suitable for generating an incident alert to nearby AEDs and volunteer responders in response to a request for public AED assistance.

When a cardiac arrest incident occurs, the AED response network server 20 may receive a request for assistance. The request for assistance can come from a variety of different sources, including from an emergency services server 25 (directly or indirectly through an emergency services interface), a user app 35, from virtual assistants, from devices capable of detecting sudden cardiac arrest incidents or from any other suitable system. FIG. 2 is a flow chart illustrating a flow suitable for conveying alerts to nearby public AEDs and public responders in the event of a potential cardiac arrest incident in accordance with one embodiment.

When a request for assistance is received (step 201), the AED response network server 20 attempts to identify and select one or more registered volunteer responders and/or volunteer responder devices that are nearby the incident (step 204). The AED response network server also attempts to identify and select one or more known connected AEDs that are nearby the incident (step 209). The protocols, processes and algorithms used to identify suitable volunteers and AEDs may vary widely and a few suitable approaches are described in U.S. Pat. No. 10,565,845 (P014A); U.S. Pat. No. 10,621,846 (P014C1); U.S. Pat. No. 10,957,178 (P014X1); U.S. Pat. No. 11,138,855 (P014X2) and U.S. patent application Ser. No. 62/834,137 (P017P) and Ser. No. 62/928,329 (P017P2), each of which is incorporated herein by reference.

The AED response network server then sends an emergency incident nearby alert to the selected registered volunteer responder(s)/devices that are close to the incident (step 211). The alert may be sent via any of a variety of different messaging technologies, including Apple IOS and Android push notification services, SMS text messages, other text or voice messaging protocols, multimedia messaging protocols (e.g., MMS), instant messaging or iMessage technologies, e-mail, etc. If a volunteer responder is nearby that either (a) has an AED or (b) can readily access an AED, then they can grab an AED and quickly bring the AED to the scene of the incident. In many situations, such a volunteer responder who has an AED, or knows the location of a nearby AED, may be able to bring an AED to the scene quicker than it would take a bystander at the incident to try to locate and fetch an AED or the time it takes EMS to arrive. The emergency incident nearby alert may be sent to any devices associated with the volunteer responder(s) that have been designated to receive such messages. Often this will be a Smartphone or similar mobile communication device. However messages may be sent to any of a number of other types of devices in addition to, or in place of, a Smartphone, as for example, a tablet computer, a PDA, a smart watch, a smart speaker, a virtual assistant, a security system (e.g., a home, office, neighborhood or community security system), etc.

It should be appreciated that volunteer responder devices are not limited to devices associated with a specific individual. For example, the security guard station of a hotel, business, country club, living community, etc. may have a connected device that is registered to receive incident notification pertinent to their establishment or community. In another example, a home security network may be registered to receive incident notifications. Of course, there are many other examples as well.

In parallel with the notification of any nearby volunteer responders, emergency alert notifications may also be sent directly to any connected AEDs 10 that are close to the incident (step 213). As explained in some of the incorporated patents, the notified AED can issue an emergency nearby alert signal meant to attract the attention of personnel or bystanders nearby the AED of the incident and request that they bring the AED to the incident location. Typically, such messages would only be sent to connected AEDs that have opted into the AED responder network.

In some embodiments, at least some of the AEDs 10 can be queried to report their current functionality status and current location. When such capabilities, exist, each of the AEDs that are believed to be nearby the incident can be queried (pinged) to provide its current status/location as part of AED identification step 209. Each of pinged AEDs then responds giving its current status and location information and that current information can be used to help determine which AEDs to send an emergency incident alert to in step 213. A few approaches for selecting a subset of AEDs to notify out of a larger responding set of AEDs are described in the incorporated U.S. Pat. Nos. 10,565,845 (P014A); U.S. Pat. No. 10,621,846 (P014C1); U.S. Pat. No. 10,957,178 (P014X1); U.S. Pat. No. 11,138,855 (P014X2) and U.S. patent application Ser. No. 62/834,137 (P017P) and Ser. No. 62/928,329 (P017P2).

After emergency nearby alerts have been sent to any nearby registered volunteer responders and/or registered connected AEDs, the AED response network server can communicate with any responder(s) that agree to respond to the incident as appropriate to help guide them to the location of the incident and convey other information that may be helpful in responding to the incident (step 215).

It should be appreciated that there are a number of scenarios where causing the AED to issue an emergency nearby alert may result in a defibrillator and possibly even a trained responder arriving at the site of a cardiac arrest incident faster than would otherwise occur. For example, in many circumstances a defibrillator may be positioned at a location that is near a designated responder—as for example, in the context of a school setting, the defibrillator may be positioned near (or in) the office of a coach, administrator, nurse or teacher that is a trained responder. In the context of an office building, the defibrillator may be positioned near an owner, administrator or other employee that is a trained responder. When the AED issues an alert, the alert may be heard by the trained responder. In such circumstances there is significant value to notifying the potential responder(s) of an emergency incident that may require a defibrillator in real time so that they can go to the scene and provide assistance as needed. Even when a designated responder (or registered volunteer responders) is not immediately available, there may be other responsible personnel near the location of a defibrillator and the alert generated by the AED will notify such personnel of the occurrence of a cardiac event in their vicinity that they may be able to help respond to. Again using the context of a school setting, other administrators, teachers, coaches or other responsible personnel that happen to be near the defibrillator at the time an incident can be encouraged to quickly take the defibrillator to the location of the incident. Still further, there is even value to informing bystanders (e.g. fans at a sporting event, students or visitor in the school, bystanders in a public space, etc.) that a defibrillator is needed at a nearby emergency incident since it is possible that such a bystander will be motivated to take the AED to the location of the emergency. Although the examples above focus somewhat on the context of a school, it should be appreciated that the same motivations apply in a wide variety of different scenarios.

As previously discussed, when the AED response network server 20 receives a request for assistance (e.g., step 201 of FIG. 2) or otherwise determines that a volunteer responder may be useful in a particular situation, the server will try to identify nearby AEDs and/or nearby volunteer responders (e.g., steps 204 and 209 of FIG. 2). There are a wide variety of selection protocols that may be used to identify potential AEDs and responders.

As discussed above, some connected AEDs have the ability to report their current status and current location. The location can be identified based on any of a wide variety of location services that may be available to pinpoint the location of the AED including: Global Navigation Satellite System (GNSS) (e.g., GPS) chips within the AED or an interface unit attached to the AED; cellular or Wi-Fi locating technologies; metropolitan beacon systems; etc. In such embodiments, the AED response network server can ping each of the connected AEDs that are believed to be within a designated distance or response time of the patient. As suggested above, the designated distance may be within a defined radius from the incident (e.g. a relatively large radius), or may be based on more sophisticated measures such as whether the device is identified as a static device that is expected to normally be kept in the same place, or a mobile device that may be expected to be moved around (e.g., placed in a vehicle or carried around by its owner). Alternatively, when available, estimated response times can be used.

The queried AEDs each communicate their functionality status and location to the AED response network server to inform the server as to whether they are in adequate operating condition to be utilized on a patient, otherwise defined as "functional AEDs." Once AED response network server 20 identifies the functional AEDs within a defined distance of the patient, the server 20 sends an emergency alert (step 213) to any such AEDs deemed appropriate. It is important to note that if any of the AEDs communicate with the AED response network server that they are not in adequate operating condition, otherwise defined as "non-functional AEDs", the server may eliminate these AEDs from consideration and not send these AEDs an emergency alert. The emergency alert that a "functional AED" receives activates an audible and/or visual signal on the identified AEDs (referred to as a "Nearby Incident Alert") signifying that there is an emergency situation for which bystander assistance would be helpful. If a bystander notices the alert, they can "accept" the emergency indicating a willingness to bring the AED to the scene, a map and/or directions is/are displayed on the AED that the responder can use to navigate to the patient's location. Additionally, or alternatively, audible directions may be provided to the user.

A variety of different factors can be considered in determining which AEDs are notified of a nearby incident. In some embodiments, certain functionality related status characteristics are included. For example, a unit with a low battery or expired pads or a unit that is outside of the recommended operating temperature may be assigned a lower priority, but may still be selected for notification if it is otherwise the best or only option.

Somewhat similarly, if a volunteer responder accepts an emergency, a suitable map and/or directions may appear on the volunteer's responder device 40 (e.g., Smartphone) and guide the volunteer responder as appropriate. In other circumstances the destination (e.g., a destination address or other identifying information) may be additionally or alternatively provided so that the volunteer responder may enter the destination in their own directions app as desired.) It should be appreciated that there may be several communications back and forth between the AED response network server 20 and the volunteer responder as appropriate. For example, the responder may be asked whether they have immediate access to an AED. If so, a map may be displayed on the responder device to guide the volunteer directly to the incident. If not, the map may display the location(s) of available AEDs and guide the volunteer to a functional AED that is the closest to being on the way to the incident and then to the incident itself so that the volunteer can bring the AED.

When desired, the AED response network server can also intelligently direct volunteer responders in a coordinated manner For example, if a volunteer that saw an emergency nearby alert on an AED has affirmatively indicated that they are responding to the incident by bringing the AED, a registered volunteer responder who is closer to the incident but doesn't have an AED in hand may be directed to proceed directly to the incident rather than diverting out of their way to find an available public AED. Of course, the specific protocols and priorities utilized in directing multiple volunteer responders can vary widely based on the priorities and design goals of the responder network management. This can include decisions regarding: how many volunteers and/or AEDs to send incident notifications to; when to call off additional potential responder(s) in the event that one or more other responders have affirmatively indicated that they are responding to the incident; when to terminate further broadcasts of an incident alert (e.g. due to professional emergency medical personnel arriving on the scene, or due to responses by other); how many AEDs to try to bring to an incident; whether and in what circumstances volunteer responders may be directed to travel directly to an incident even if they don't have an AED in hand; etc.

Figure 3:
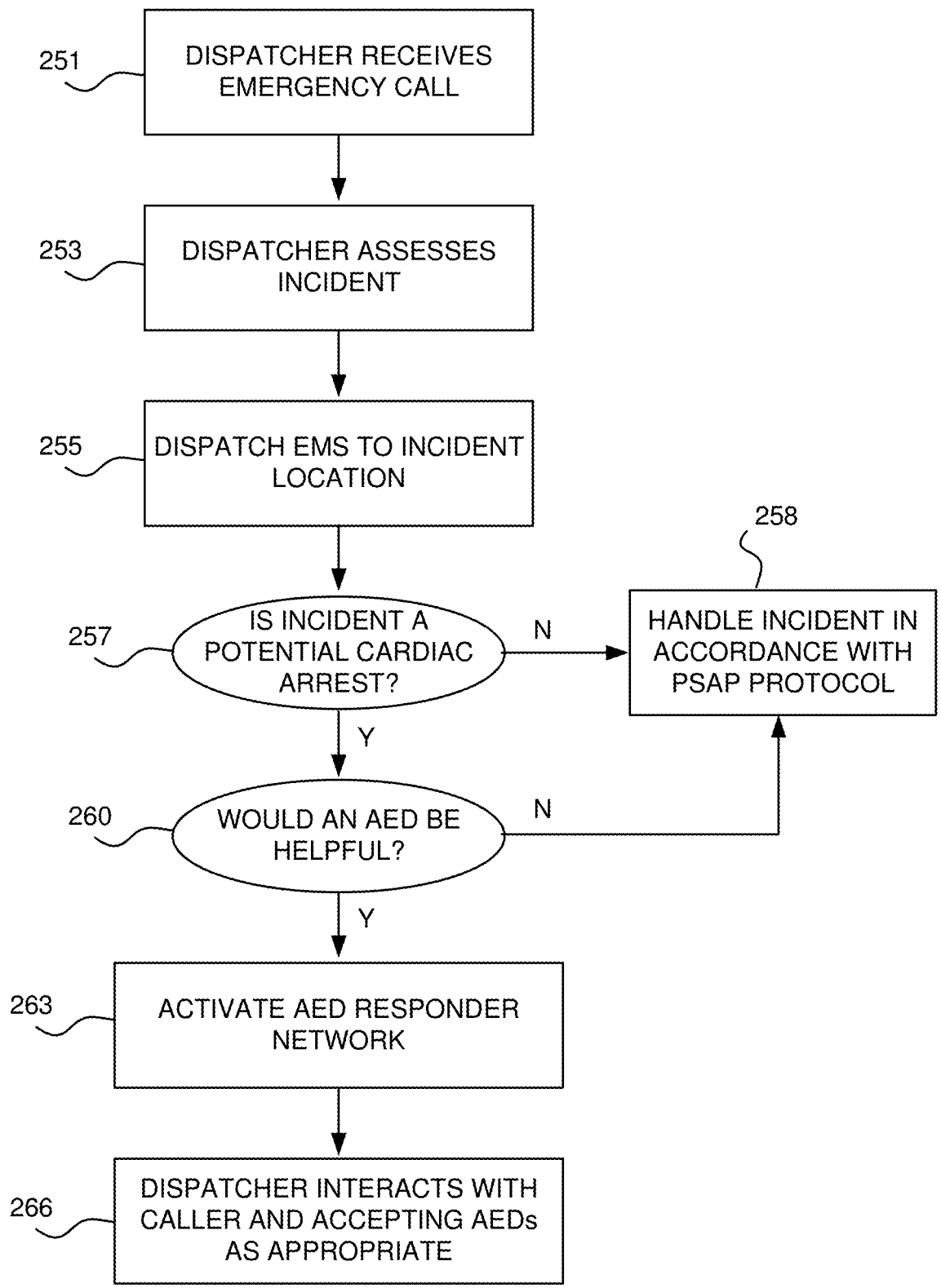
FIG. 3 is a flow chart illustrating a flow for a PSAP dispatcher activating an AED responder network.

There are a number of ways that the initial request for assistance (201) can be triggered. By way of example, a few suitable responder network triggering approaches are described in U.S. Pat. No. 10,957,178 (P014X1) and U.S. patent application Ser. Nos. 17/007,787 (P020A); Ser. No. 17/100,313 (P20B); each of which is incorporated herein by reference. Of particular relevance to the present disclosure are requests for assistance that are triggered by a PSAP operator/dispatcher. One such dispatcher-initiated responder network initiation workflow is illustrated in FIG. 3. Representative CAD side user interfaces suitable for use is such a workflow are illustrated FIGS. 4-6.

FIG. 3 is a flow chart illustrating a flow suitable for generating an alert to nearby public responders and AEDs that is initiated based on a call made to an emergency operator at a PSAP in accordance with one embodiment. In the illustrated embodiment, the process begins when an emergency notification (e.g., a 911 call, a notification from a monitoring device, etc.) is made and routed to the PSAP responsible for the area from which the call originated. The call/notification is answered by an emergency operator (e.g. a 911 dispatcher/telecommuicator) as represented by block 251. The call is often made by a witness or bystander to a potential cardiac arrest incident and the call effectively initiates the emergency response process. Regardless of whether the caller witnessed the cardiac arrest incident or is told to call emergency services by another party, calling for help ensures professional first responders are dispatched to the emergency as quickly as possible.

Although it is expected that in most circumstances, the call to emergency services will be initiated by a person, in some instances, the call may be automatically initiated by a device which has detected a scenario which appears to be a potential cardiac arrest incident or via other suitable mechanisms.

When the PSAP dispatcher/operator answers the phone, the operator typically assesses the type of emergency that the caller is calling about, as well as the nature of the incident (as represented by block 253) in order to determine what, (if any) emergency services resources should be deployed to the incident. The assessment typically includes determining or verifying the location of the incident. When appropriate, the operator will dispatch emergency services to the scene as represented by block 255.

As part of the assessment of the incident, the dispatcher may determine that the patient has potentially experienced a sudden cardiac arrest as represented by decision block 257. Some key indicators of sudden cardiac arrest include descriptions of the patient being unresponsive and not breathing normally.

When cardiac arrest is suspected, the dispatcher has the option to activate the AED responder network as represented by decision block 260. Typically, it would be desirable to activate the AED responder network when no AED is present at the incident location and/or in other circumstances in which an AED and/or the assistance of a trained volunteer might be helpful.

Figure 4:
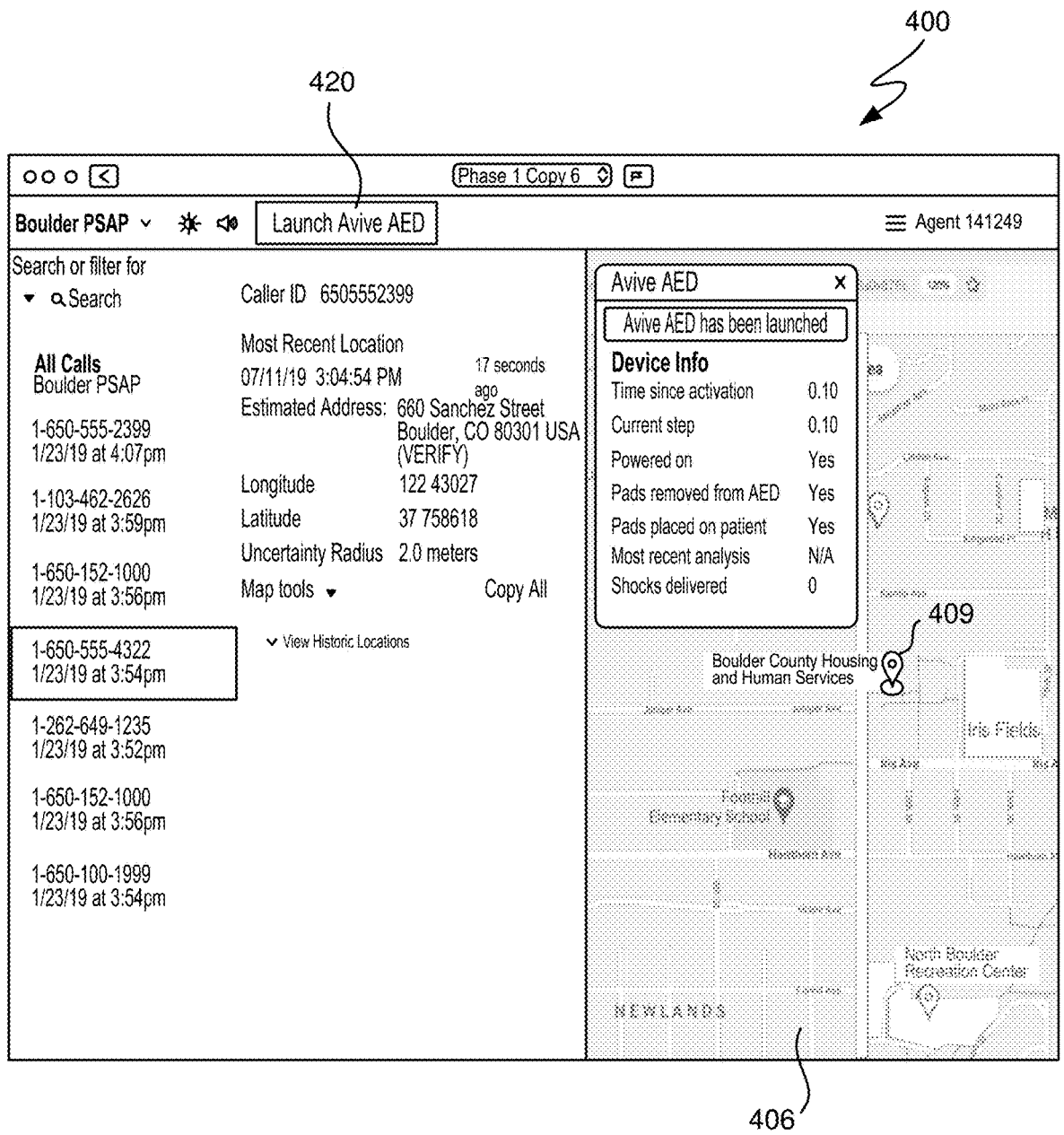
FIG. 4 is a screen shot of a representative dispatcher user interface that includes a responder network activation GUI widget and a map showing the incident location.

The mechanism(s) by which the dispatcher activates the AED responder network may vary widely. A variety of user interfaces may be provided to enable the dispatcher to active the responder network. Often such a request will be initiated by selecting an appropriate GUI button or other GUI construct on the CAD system display. By way of example, one suitable dispatcher user interface is illustrated in FIGS. 4 and 5 and discussed in more detail below. Once the AED responder network has been activated, the dispatcher communicates with the caller and/or any accepting responders as appropriate given the incident and surrounding circumstances as represented by block 266.

It should be appreciated that most calls to emergency call centers do not relate to potential cardiac arrest incidents and therefore there is no reason to activate the AED responder network. For instance, if the emergency is described as a house fire or a burn victim, an AED typically wouldn't be useful. In such circumstance, the dispatcher would handle the call in a normal manner without activating the AED responder network and following the PSAPs standard protocols as represented by block 258. Since the subsequent operator actions are not particularly relevant to the present disclosure, the process is effectively done from the standpoint of the AED responder network.

A computer-aided dispatch (CAD) system, and/or an emergency services interface portal (ESI) portal (e.g. a RapidSOS, RapidDeploy or similar portal), and/or a responder network portal at the dispatcher's workstation will typically have a map that is displayed to the dispatcher. Often, the incident location will be displayed on the map. In some implementations, the location from which the received emergency call is being made will be automatically marked on the map based on the default presumption being that the location from which the call originated is fairly representative of, or reasonably close to, the location of the incident being called about. As will be appreciated by those skilled in the art, there are a number of technologies that can be used to automatically detect the location from which a call is made. Additionally, or alternatively, the location displayed on the map may be based in whole or in part on location information entered by the operator.

FIG. 4 illustrates a representative dispatcher user interface (dashboard) 400 suitable for facilitating dispatcher interactions with an AED responder network. In the embodiment of FIG. 4, a dispatcher display screen displays a window having a map 406 that preferably shows the location of the incident 409. In various implementations, the dispatcher display screen may be part of a CAD system, an ESI portal, or other appropriate system. The user interface also includes a GUI widget such as GUI button 420 that the operator may select to initiate activation of the volunteer responder network. Of course, a variety of other GUI constructs can serve as the volunteer responder network activation mechanism in other embodiments.

Figure 5A:
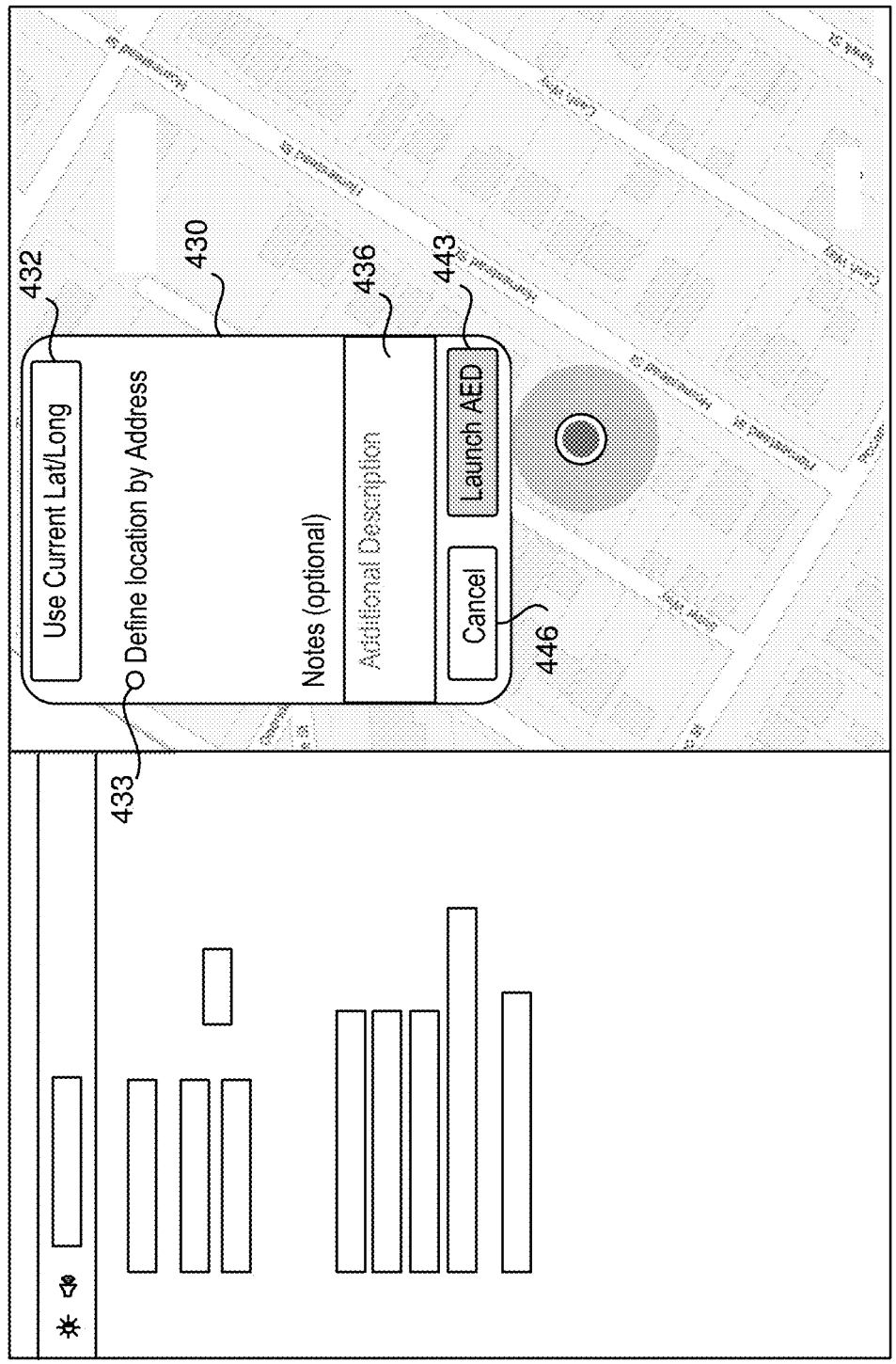
FIGS. 5A-5C are screen shots of a representative dialog box that permits a dispatcher to enter or select an incident location and/or enter notes to be transmitted to a responder network.

In some implementations, selection of the GUI widget (e.g., GUI button 420) alone causes an Activate AED Responder Network message to be sent directly or indirectly to the responder network server 20. In other embodiments, it may cause a dialog box to appear on the screen. One such dialog box 430 is illustrated in FIG. 5A. In still other embodiments, a small responder network initiation dialog box (e.g., a box analogous to the dialog box shown in FIG. 5A) may be more persistently displayed on a screen so that it is always immediately accessible to the dispatcher. In the illustrated embodiment, the dialog box 430 includes GUI widgets 432, 433 that allow the dispatcher to either utilize the incident location currently identified in the CAD system (Use Current Lat/Long button 432) or to indicate a desire to enter a different address (check box 433). Checking box 433 causes a location entry dialog box 435 to appear on the screen to allow the dispatcher to enter the desired location as seen in FIGS. 5B and 5C.

In the illustrated embodiment, the dialog box 430 also includes a notes entry box 436 that allows the dispatcher to provide notes relevant to the incident that might be helpful to volunteer responders. That could include notes relevant to navigating towards the incident—e.g., "you'll see a white van parked in front of the house" or any other appropriate information.

The illustrated embodiment also includes a dispatch button 443 and a cancel button 446. Selection of the dispatch button 443 causes an activate AED responder network message to be sent (directly or indirectly) to the responder network server. Selection of the cancel button closes the dialog box 430 without sending an activate AED responder network message.

Figure 5B:
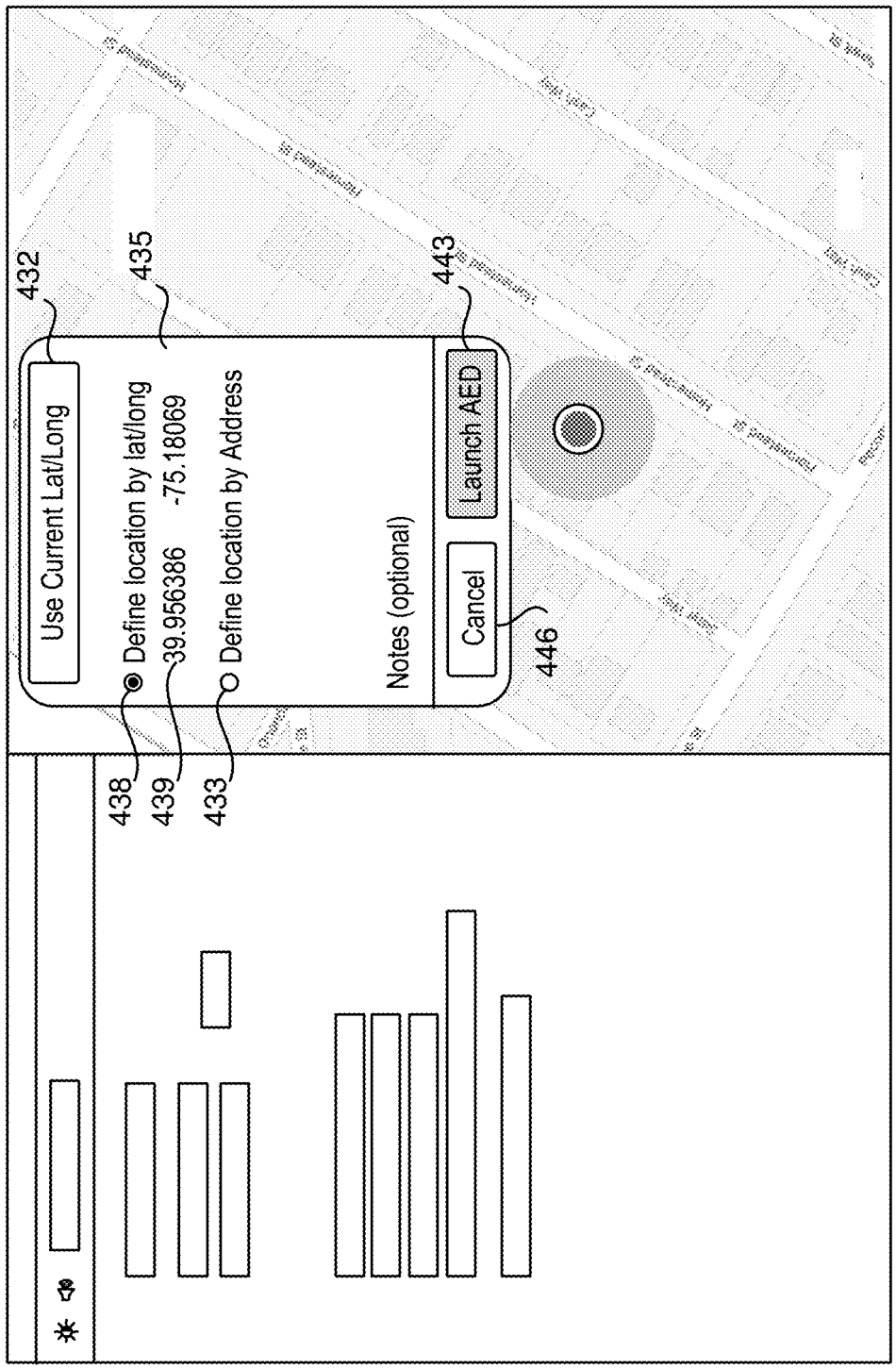
Figure 5C:
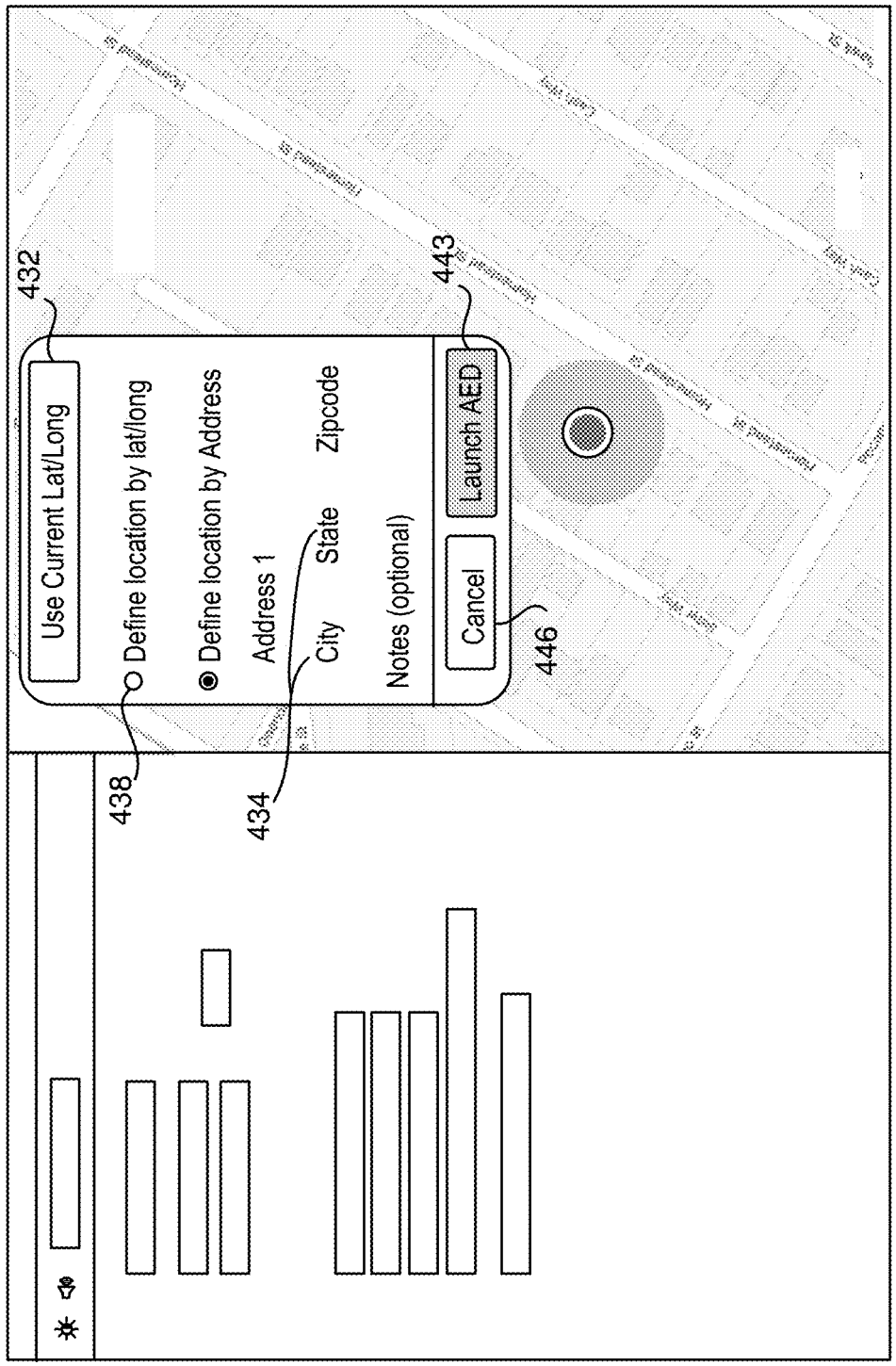

As seen in FIG. 5B and 5C respectively, in the illustrated embodiment, the location entry dialog box 435 permits the dispatcher to define the location of the incident by either its latitude/longitude (check box 438 and related latitude text entry boxes 439) or by address (check box 433 and related address text entry boxes 434).

Although a specific user interface for facilitating dispatcher originated AED responder network activations has been shown, it should be appreciated that the specific user interface may take a wide variety of other forms. In a specific alternative example, a dialog box (which may be either persistently displayed or pop up in response to the selection of a GUI widget such as launch button 420) includes three check boxes, a notes entry box and a dispatch button. The first check box has an associated Address entry box for entering an address (e.g., a street address) for the incident. The second check box has associated Latitude and Longitude entry boxes that allow the dispatcher to enter the geocoordinates (e.g., latitude and longitude) of the incident. If desired, selection of the latitude/longitude check box can cause the latitude and longitude of the active incident to be auto-filled into the Latitude and Longitude entry boxes. The third check box is a "Use map to set location" check box. When selected, the dispatcher can select a location on a/the map displayed on a screen and the coordinates of the selected location are used as the location of the incident. In some embodiments, the map that the dispatcher selects the location on may be a map that appears in response to selection of the associated check box. In others, it may be a map already displayed on the screen.

The notes entry box allows the dispatcher to enter notes to be provided to responders as previously described. Selection of the dispatch AEDs button causes the Activate AED Responder Network message to be sent to the network server, thereby activating the AED responder network.

The Activate AED Responder Network message may take a variety of different forms, but typically it includes a least an indication of the location of the incident. Optionally the Activate Responder Network message may other useful information such as one or more timestamps, dispatcher notes (if any), an emergency notification type identifier, emergency type identifier, a PSAP identifier, a security key, etc. In some embodiments, the Activate AED Responder Network message has a number of predefined fields that hold such information—e.g., a notification type field, an emergency type field, a location field, one or more timestamp fields, a dispatcher notes field, a PSAP identifier field, a security code field, etc.

The location may be provided in any suitable form, as for example the geo-coordinates—e.g., latitude, longitude and altitude (if available), GNSS coordinates, a street address or other suitable identifying locating information. The location may also include a confidence radius indicative of how precise the location is believed to be (e.g. +/−20 feet).

The dispatcher notes may be freeform text or other suitable information entered by the dispatcher—e.g., "Apartment 2B, enter via gate on left side of the building, etc.

Various timestamps may be included, as for example a timestamp indicating when the message was sent, a timestamp indicating when the initial emergency call or notification was received by the PSAP, etc.

The PSAP identifier indicates which PSAP the incident is being routed from. The security key may be used by the receiving responder network to help filter out spam and/or malicious attacks.

The emergency type may indicate the nature of the emergency incident (e.g., that the incident is a potential sudden cardiac arrest). The emergency type field is expected to be particularly useful in responder networks that extend beyond responding to just sudden cardiac arrest, as for example to include responses to other incidents such as poisonous bites, opioid overdoses, allergic reactions (anaphylaxis), bleeding incidents, etc. In the sudden cardiac arrest area, the emergency type can also be used to indicate that only CPR is require (e.g., as may be the case if an AED is known to be at the scene but a trained volunteer responder would be helpful).

The emergency notification type indicates the nature of the message. Such a field is particularly useful when the Activate Responder Network is just one of a number of different types of Network Notification messages that a PSAP may send to a Responder Network. For example, one type of Network Notification message that may be sent from the PSAP is the initial emergency notification (referred to as the Activate AED Responder Network message above). Another emergency Network Notification message type may be an update to an existing emergency. Updates are useful in a number of circumstances, as for example, when the dispatcher is able to provide more detailed directions or information about the incident or if the incident location changes due to information that later becomes available to the dispatcher. Another Network Notification message type is a cancel emergency message—which may be appropriate for a number of reasons, as for example when EMS has arrived at the scene, if sufficient volunteer responders have arrived at the scene, if the dispatcher realizes that the incident is not a cardiac arrest, etc.

Upon receiving an Activate AED Responder Network message the AED responder network server preferably replies acknowledging receipt of the activation message. In parallel the AED responder network server 20 may ping selected AEDs 10 that are nearby the incident as discussed above with reference to FIG. 2. When desired, the responder network server may also ping nearby responders, responder devices, user devices, etc. The pinged AEDs respond with an indication of their current status and current location and any other desired/appropriate information. The responder network server preferably also sends Nearby Incident messages to volunteer responders and/or volunteer responder devices that are in the vicinity of the incident. Some such approaches are described in some of the incorporated patents, including U.S. Pat. No. 10,957,178.

Figure 6A:
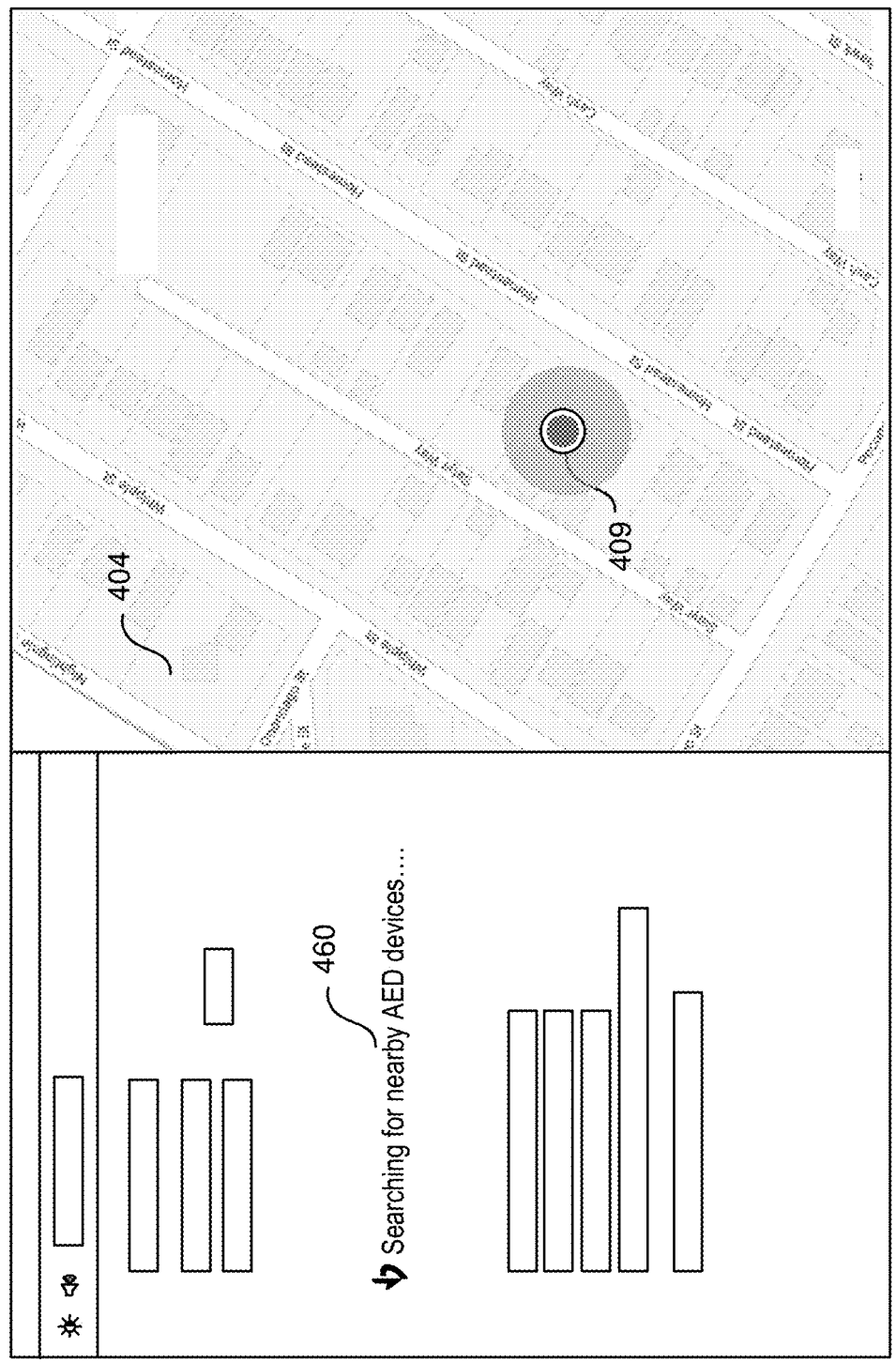
FIGS. 6A-6D are screen shots of a representative dispatcher user interface showing the rendering of icons representing AEDs and accepting volunteer responders in the vicinity of an incident.

After receiving confirmation of the location and operational status of one or more AEDs, the AED network server may send a message to the dispatcher terminal providing the confirmed location of one or more of the responding AED. For each AED identified in the message, the user interface at the dispatcher terminal can then display an AED icon 440 that represents the associated AED at the corresponding location in map 405. As more nearby AEDs respond, additional AED location confirmation messages may be sent to the dispatcher terminal and corresponding AED icons 440 are rendered at the appropriate location(s) on the map 405 as seen in FIG. 6A. Similarly, when other resources respond, appropriate location confirmation messages may be sent to the dispatcher terminal and corresponding resource icons may be rendered for those resources as well. In some embodiments, these location confirmation messages are sent in the form of a Resource List as described in more detail below. However, in other embodiments, a variety of other message structures may be used. It should be appreciated that in many embodiments, the AED responder network server may filter the responding resources and only report a few selected resources to the PSAP as will be discussed in more detail below. For example, in some embodiments, only the location(s) of the very closest AED(s) and resources that have accepted the incident may be shown. In other embodiments greater numbers of nearby resources may be shown.

In some embodiments the AED responder network server 20 is further configured to send messages to the PSAP that provide a high-level indication of the current response network status. Corresponding messages are then displayed on the dispatcher user interface as appropriate. For example, in some implementations, the high-level responder network status messages may include states such as: (i) "Searching for nearby AEDs"; (ii) "AED(s) found, not accepted yet"; (iii) "No AEDs found"; (iv) "AED(s) accepted" (v) "Volunteer responder(s) accepted"; (vi) AED activated; etc. In some embodiments, the dispatcher user interface is configured to always display an appropriate responder network status message. In some circumstances it may be desirable to display more than one status message (e.g., AED accepted and Volunteer accepted). Some of these responder network status messages are illustrated in FIGS. 6A-6D.

FIGS. 6A-6D are screen shots of a representative user interface (dispatcher dashboard) showing what the dispatcher map may look like in some implementations. FIG. 6A shows dispatcher map 404 in a state in which the AED responder network has just been launched, and the AED responder network server 20 has begun searching for nearby AEDs. At this stage, no AEDs have been identified to the dispatcher yet, but dialog box 460 displays a responder network status message indicating that the system is searching for nearby AEDs.

Figure 6B:

FIG. 6B represents a state shortly thereafter in which a nearby AED has been identified and AED icons 440 are displayed on map 404 to represent the location of nearby AEDs for which the location and operational status are known and/or have been confirmed. In the illustrated scenario, a single AED has been shown, but it should be appreciated that when available, other nearby AEDs may be represented on the map as well. Since an AED has been located, responder network status dialog box 460 is updated to indicate that one or more AEDs have been found, but that no AEDS have accepted the incident at this point.

Figure 6C:

FIG. 6C is a screen shot similar to FIG. 6B showing that the represented AED has "accepted" the incident. Since an AED has now accepted the incident, the responder network status dialog box 460 is updated to indicate that at least one AED has now accepted the incident. Although difficult to see in the gray scale drawings, preferably, the visual appearance of the icon representing the accepting AEDs has changed and is therefore represented by the label 441 instead of 440. In the illustrated embodiment, the color or color scheme of the icon has changed. In other embodiments, the visual appearance may additionally or alternatively change in other ways, as for example by changing one or more of the size, shape or graphics of the AED icon. In this way AEDs that have accepted the incident have a different visual appearance than other nearby AEDs that have not accepted the incident, thereby making it easy for the dispatcher to understand which AEDs (if any) are on their way to the incident. Although not shown in the screenshot of FIG. 6C, it should be appreciated that often multiple AEDs may be represented on the dispatcher map 404 and at any given time, some may not have accepted the incident and are therefore represented by corresponding icons 440, whereas one or more others may have accepted the incident and therefore are represented by icons 441.

Figure 6D:
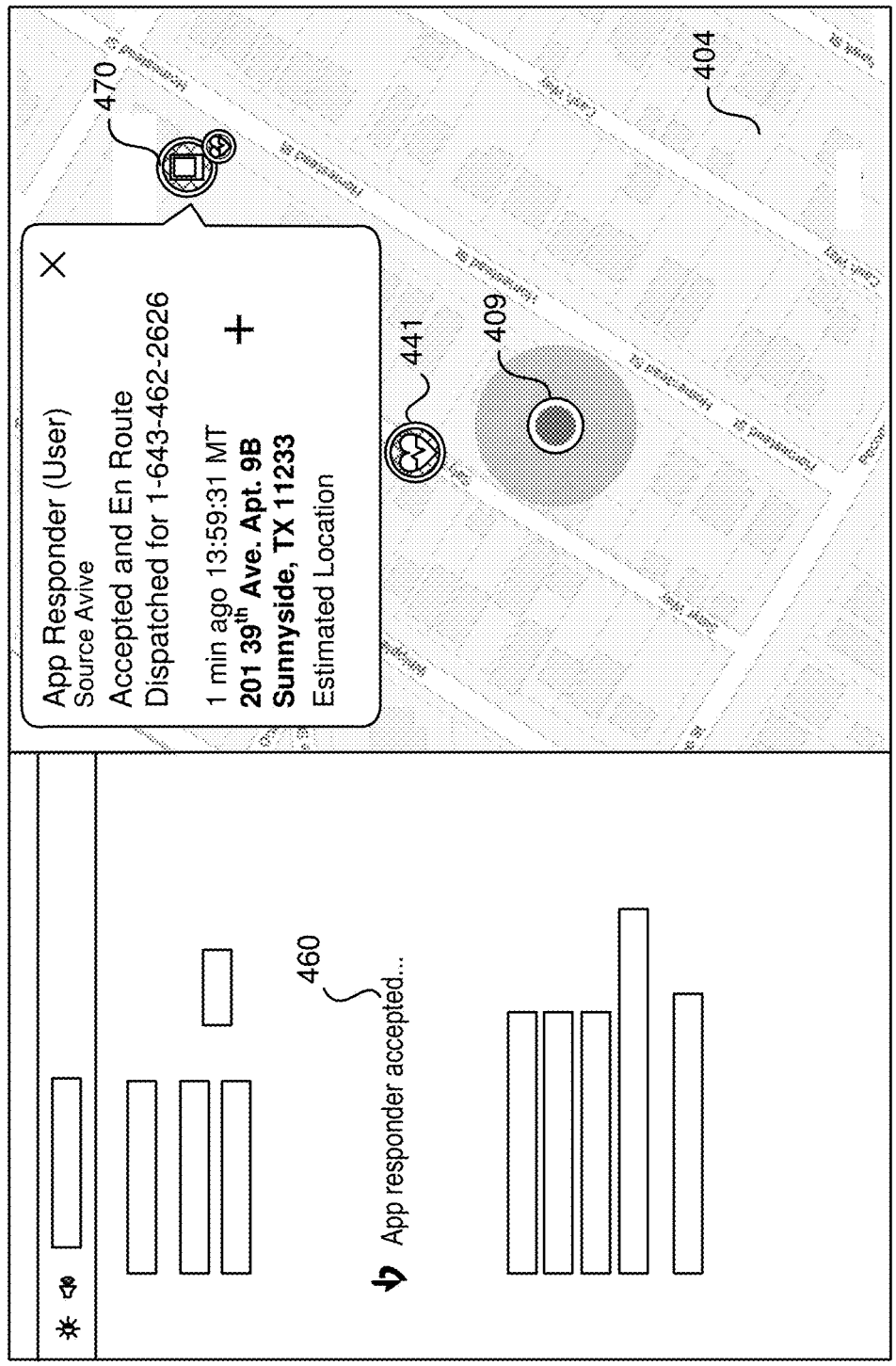

FIG. 6D is a screen shot similar to 6C a bit further into the incident response. At this stage, two notable things have happened. First, the AED represented by icon 441 is traveling towards the incident and its location on the map has been updated to show its current location/last reported location. In this way, the dispatcher can readily track the progress of the corresponding AED towards the incident and provide appropriate instructions to the caller in response thereto. An example of that type of instruction may be something like, "a responder with an AED is approaching your house, please go open the door and let them in."

FIG. 6D also shows that a volunteer responder (referred to as an App Responder) has also accepted the incident. The responder network status dialog box 460 has been updated to show that a volunteer responder has accepted the incident. An icon 470 is displayed on the map to show the current location of the volunteer responder. Again, the location of the icon 470 on map 404 will be updated as the responder moves towards the incident. It can also be seen that the icon 470 representing the volunteer responder has a different visual appearance than the icons representing the AEDs 440, 441. The different visual appearance can be one or more of a different icon graphic or shape, a different icon size and a different icon color scheme. Optionally, the dispatcher may obtain information about the volunteer responder by selecting (e.g., clicking on) the corresponding icon 470. In the illustrated embodiment, when the dispatcher clicks on the icon 470, a dialog box 474 appears which provides information about the responder. Although representative information is shown, it should be appreciated that the information about the responder may vary widely based on network design preferences. By way of example, in some circumstances, the information presented may include the responders name and/or information about the responders experience—e.g., Rob is trained in CPR; Mary is an off duty EMT, etc.

As suggested above, when appropriate, the map may show the location of any combination of device (e.g. AED) locations, devices (e.g., AEDs) that have accepted the incident, and volunteer responders. In some preferred embodiments, only volunteer responders that have accepted the incident are shown, however, is should be appreciated that in other embodiments responders that have not accepted the incident may be shown as well. When volunteer responders (or other devices) that have not accepted the incident are shown, it may be desirable to visually distinguish between volunteers/devices that have accepted the incident, vs. those who have not yet accepted the incident.

Figure 7:
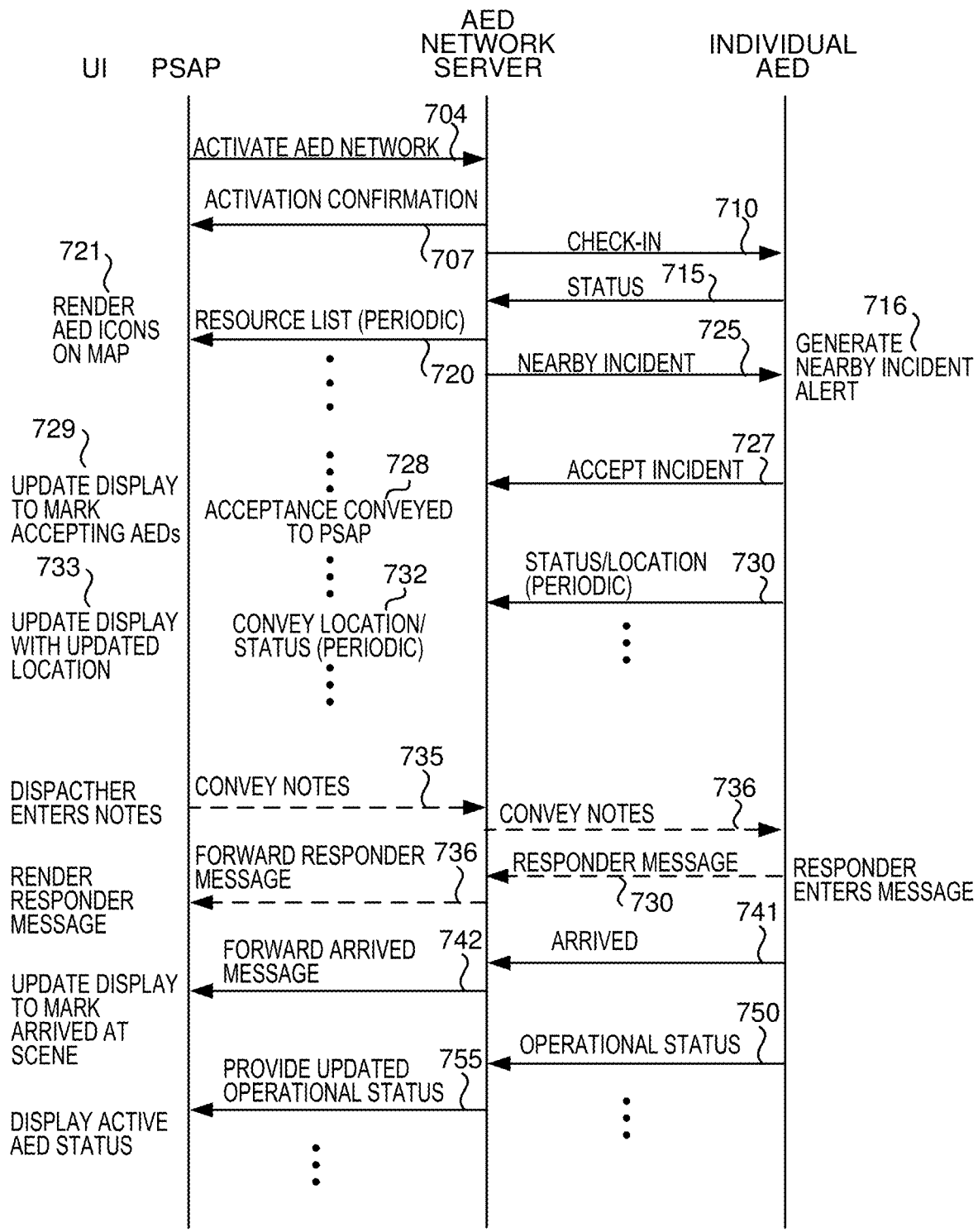
FIG. 7 is a message timing diagram illustrating a few representative messages that may be conveyed between the PSAP, the AED Network Server, and/or selected AEDs in the AED responder network.

FIG. 7 is a diagrammatic message timing diagram that show selected representative messages that may be conveyed back and forth between the PSAP 25, the AED network server 20 and selected AEDs 10. The illustrated messages support many of the frameworks, methods and user interfaces described herein.

As discussed above with respect to FIG. 2, when the dispatcher requests activation of the AED network, an Activate AED Responder Network message 704 is transmitted (directly or indirectly) to the AED network server 20. The Activate AED Responder Network message preferably includes an indication of the geo-location of the incident as well as any notes (e.g., notes 437) that may have been entered by the dispatcher prior to activating the responder network. Optionally, the AED network server replies to the Activate AED Responder Network message 704 with an Activation Confirmed message 707.

When the AED network server receives an Activate AED Responder Network message it does a number of things. Generally, these may include tasks such as (a) informing AEDs and/or volunteer responders and/or other connected devices (collectively referred to as "resources") that are close to the incident that there is a nearby cardiac arrest incident for which their assistance; and (b) informing the PSAP of resources that are located near the incident.

In some embodiments, the server 20 maintains a device database that includes records for each of the AEDs and other resources in its network. Some of the information stored about the AEDs may include information such as: (a) the device's geo-location; (b) whether the AED has been designated as a private AED or a public access AED; (c) whether the AED's administrator has opted in to receiving notifications regarding nearby potential cardiac arrest incidents; (d) whether the AED is designated as a mobile AED or is expected to be stored at a fixed location; (e) the current status of the defibrillator, etc. Preferably, the status and location information is updated on a regular basis, as for example as a result of periodic (e.g., daily) self-test status checks that are reported by the AED to the server 20.

When the AED is designated as a public access AED, the devices owner/administrator may designate the hours/days/etc. that it is available to the public. For example, if the AED is located inside an office building or retail establishment that is only open during designated hours, it may be desirable to indicate that the AED is only publically available during those hours so that potential $3^{rd}$ party responders don't try to find an AED in a locked building.

In general, Nearby Incident messages may be sent to any AED that has opted in to such notifications. That may include both public access AEDs that are available to the general public, and private AEDs which may not be advertised as being available to the general public. There are many circumstances where a private AED may elect to receive notifications of nearby incidents. Once such example may be when the AED is a personal AED of a volunteer responder. Another such example may be when the AED is located in a building or complex that is not publically accessible. Another example is when the AED is located in a person's home.

An AED may also be designated as a fixed location AED or a mobile AED. Fixed location AEDs are expected to be stored at the same location all/most of the time. In contrast, mobile AEDs are expected to be moved more often. Some representative examples of mobile AEDs might include AEDs expected to be kept in a vehicle or carried as part of a safety kit (e.g., by a coach, guide or volunteer responder).

It is expected that most public access AED would be fixed location AEDs that are expected to be stationed at a fixed location (e.g., in an AED cabinet at an office building, at a field, at a designated location in and airport, etc.). However that is not a requirement, for example, a police department might choose to designate AEDs carried in police vehicles as mobile, public access AEDs so that their locations can be displayed on an AED map in the event that the officer happens to be nearby when a potential cardiac arrest incident occurs. Of course, in other circumstances it may be desirable to designate such devices as private.

Upon receipt of the Activate AED Responder Network message, the AED network server identifies a set of AEDs that are potentially available to use in responding to the incident. The set of potentially available AEDs may be determined in a variety of ways using a variety of different filtering techniques. In some embodiments, the set of potentially available AEDs is determined at least in part by identifying the AEDs in the responder network database that are understood to be within a designated range of the incident based on the last known location of the AED as stored in the device database. In some implementations, the fixed range threshold is used in all circumstances, while in others the designated range threshold may vary based on a variety of factors. For example, in some implementations, an estimated "response time" (e.g., an estimation of the time that it will take for the AED to be carried to the incident scene) may be used instead of a designated distance. In another example, the permissible range allocated for devices registered as mobile AEDs may be larger than the range allocated for permanent AEDs. This can be desirable because a mobile AED that is located in a vehicle may have traveled quite far since it last reported its status and location to the AED response server. In another example, when the incident location in a rural area that doesn't have a large number of AEDs, the range threshold may be larger than when the incident location is within a metropolitan area having a large number of registered AEDs. The specific range thresholds used in this initial identification of potentially nearby AEDs may vary widely. In some situations, this initial filtering may be quite broad (as for example, 50 or 80 miles in some applications) or it may be significantly more focused (e.g., a few miles or less) as may be appropriate for any particular setting and/or class of registered AEDs.

In some embodiments, additional or other filtering may be used to identify the set of potentially available AEDs. For example, U.S. Provisional Patent Application No. 63/093,568 (REV1P023P), which is incorporated herein by reference describes responder networks that incorporate geofencing and other responder preferences in the identification potentially available AEDs.

In the illustrated embodiment, a status query or "Check-in" message 710 is sent to each of the identified AEDs or to any desired subset of such AEDs. This is sometimes referred to as "pinging" or "polling" the AEDs. The pinged AEDs each respond by sending a Status message 715 that indicates the current location and current operational status and current location of the AED. This Check-in/Status report message PAIR is quite helpful because it serves as a mechanism for verifying the current location and operational status of the AEDs that are believed to be generally in the vicinity of the incident. This gives the AED response server the latest information about the identified AEDs and effectively verifies that communications with the devices is possible. It can also serve as a mechanism for opening a connection between the AED and the AED network server to facilitate future communications between the two. Although not shown in FIG. 7, similar status queries of check-in messages can be sent to other resources within the responder network as appropriate.

The specific status information conveyed in Status message 715 may vary widely, but it preferably includes at least the device's current location and operational status. The operational status reported may include the results of the most recent status check performed by the AED. Such a status report may be very simple (e.g., functional/non-functional) or it may include more detailed information such as (but not limited to) battery charge level, pad expiration date, recent self-test results, etc. It should be appreciated that the amount of data transferred in the original request (the "Check-in" message) and the response (the current Status message) are quite small and can therefore be transmitted back and forth quite quickly. The Check-in messages may be transmitted using any of a variety of communications protocols supported by the AEDs, including, for example, as SMS messages, as Wi-Fi or cellular communications, etc.

In some embodiments, the AED receiving a status query responds to the query by establish a connection with the AED network server 20 over a second communication channel that is different than the first communications channel over which the status query is received. The current Status message 715 is then sent over this second communication channel. In some embodiments, the first and second communications channels use different communications protocols, although this is not a requirement. For example, the status query may be sent/received using a messaging technology (e.g., SMS), whereas the connection may be established using another communications protocol such as an IP protocol (e.g., TCP/IP). There are some significant advantages to such a separate channel approach from a security standpoint as described in more detail in U.S. provisional Application Nos. 17/007,787 (P019A) and 17/007,838 (P019B), each of which is incorporated herein by reference. Although the separate channel approach works particularly well and has some distinct advantages, it is not required in other implementations.

As the AED network server receives current status messages from the pinged AEDs, it effectively develops an updated AED map with the current location and operational status of AEDs in the vicinity of the incident. It also determines which of the responding AEDs are suitable for reporting to the PSAP. The criteria that are used to determine which responding AEDs are appropriate for reporting may vary depending on the needs of any particular system. By way of example, in some implementations, any AED that is within a designated radius of the incident and is in good operating condition is reported to the PSAP. The designated radius may vary based upon a variety of factors including whether the incident is in an urban or rural area, the density of AEDs considered "close" to the incident, etc. In some embodiments, the designated radius may be dynamically adjusted based on the responses received—e.g., if no (or few) functional AEDs are within a preferred range, the range may be expanded as necessary to show the known AED(s) that are closest to the incident. In still other embodiments, the AEDs (and other resources) reported to the PSAP may be reduced to just one or a few AEDs/resources in an effort to reduce the risk of dispatcher overload. For example in some specific implementations, only the one or two closest AEDs and any resources (AEDs, volunteer responders, etc.) that have accepted the incident are presented to the dispatcher.

In some embodiments, additional or other filtering may be used to identify the set of potentially available AEDs. For example, U.S. Provisional Patent Application No. 63/093,568 (REV1P023P), which is incorporated herein by reference describes responder networks that incorporate geofencing and other responder preferences in the selection of AEDs that are sent either the initial check-in messages or the incident alerts.

Regardless of the criteria that the AED network server 20 utilizes to select AEDs to be reported to the PSAP, a Resource List message 720 is sent to the PSAP. The Resource List message 720 identifies AEDs and other relevant resources (e.g., accepting volunteers and/or other devices) that are in the vicinity of the incident and provides the location of each identified AED. The user interface 400 on dispatcher display screen 404 then renders an AED icon 440 on map 406 for each of the AEDs identified in the Resource List that are within the displayed region of the map as represented by action 721 (or an appropriate subset thereof). This allows the dispatcher to direct the caller (or other bystander) to a nearby AED that can be fetched to bring to the incident scene. A representative dispatcher map showing AED icons 440 that represent nearby AEDs is illustrated in FIG. 6A. In embodiments using the Resource List, the displayed AED icons 440 may correspond to the AEDs identified in the Resource List (or a subset thereof corresponding to AEDs in the map's field of view). In embodiments where the only resources that are included in the network are AEDs, the Resources can be considered a Nearby AED List.

It is noted that in the primary described embodiment, only AEDs whose location and operational status have been confirmed in real-time are included in the Resource List/Nearby AED List. It is believed that there are significant advantages to such an approach because it significantly reduces the possibility/probability that the caller (or other bystander) will be directed to an AED that is not actually functional or is missing from its expected location. Although real-time verification is preferred, it should be appreciated that in other embodiments, the AEDs may report their status and location to the AED network server on a regular basis (e.g., once a day, once an hour, every five minutes, etc.) and the AED network server may utilize the most recent known location/operational status of nearby AEDs when determining which AEDs to include in the Resource List. Such an approach can work acceptably well in many circumstances, particularly when the AEDs report their status on a frequent basis. Less desirable is a situation where the location of some AEDs are registered with the AED network server (or an entity that provides such information to the AED network server) but there is no effective mechanism for confirming on a frequent/regular basis that such an AED is actually present at the location and/or is in good working condition. However, since most legacy AEDs don't have the ability to electronically report their location and operational status, in some embodiments it may be desirable to include such AEDs in the Resource List as well, since such an AED may actually be the closest to the incident.

When AEDs for which the location and/or operational status has not been confirmed are included in the Resource List, it may be desirable to identify such AEDs as such, so that the icons associated with AEDs whose operational status/location have been confirmed can be rendered to have an appearance that is different (e.g., a different color, a different image, etc.) than those that have not. That allows the dispatcher to make an informed decision as to which of multiple nearby AEDs is most appropriate to send the caller to find. The temporal nature of what is treated as a confirmed status/location can vary based on system design goals. That is, in some implementations, only AEDs whose location/operational status have been confirmed in real time (e.g., in response to a status check message 710) are treated as confirmed. In other implementations, looser definitions of confirmation may be utilized (e.g., if the location/status has been confirmed within some period of time prior to receipt of the AED network activation—as for example, 5 minutes, an hour, a day, etc.).

In some implementations, the Resource List is periodically updated/retransmitted to the PSAP throughout the incident until an AED is no longer needed. Such an approach has several advantages. For example, when the AED responder network is first activated, it may take some amount of time to confirm the location of nearby AEDs. In such circumstances, updating/retransmitting the Resource List allows additional AEDs to be added to the list (and/or marked as confirmed) as those confirmations are received. Also, as will be described in more detail below, since the Resource List includes the current location of the identified confirmed AEDs, the location of the AED can be dynamically updated on the dispatchers map 406 during the incident if/as the AED is carried towards the incident—thereby providing the dispatcher with feedback that the AED is indeed on its way to the scene. As mentioned above, AEDs that have "accepted" an incident are visually distinguished from those that have not which makes it easier for the dispatcher to notice/follow the accepting AED as it is carried towards the incident. The frequency of the retransmission of the Resource List may vary widely. By way of example, in some embodiments the Resource List may be retransmitted at frequencies on the order of every 2 to 15 seconds. It may also be retransmitted any time it is updated by the AED network server 20. In a specific example, the Resource List is retransmitted every time a significant update is made to the list, and at 5 second intervals thereafter until the next update.

Since the Resource List is retransmitted regularly and/or updates as appropriate, it may be through of as a Resource Status Update message. The updates may continue as long as appropriate for the incident—e.g., until emergency services arrive on scene or until an AED is brought to the location of the incident or other suitable triggers occur.

In parallel with transmitting the Resource List message 720 to the PSAP, the AED network server may also determine which connected AEDs and/or volunteer responders to send Nearby Incident Messages 725 to. In some embodiments this selection is accomplished by an AED/volunteer selection algorithm. The specific algorithms and protocols used to select the specific devices/responders to inform of a "nearby" incident may vary widely based on a variety of factors and the perceived needs of any particular implementation. By way of example, a number of selection approaches are described in detail in some of the incorporated patent applications including U.S. Pat. No. 10,565,845 (P14A); U.S. Pat. No. 10,621,846 (P014C1); U.S. Pat. No. 10,957,178 (P014X1) and U.S. patent application Ser. Nos. 16/863,068 (P014X1), Ser. No. 62/834,137 (P017P) and Ser. No. 62/928,329 (P017P2), each of which is incorporated herein by reference.

AEDs 10 that receive a nearby incident message 725 may emit an audible and/or visual Nearby Incident Alert 726 intended to get the attention of bystanders, inform them that there is a cardiac arrest incident nearby for which the AED may be helpful and request their assistance by taking the AED to the location of the incident. Each AED that generates a Nearby Incident Alert 726 may also provide a user interface that allows a volunteer responder interacting with the AED to "accept" the incident thereby indicating their willingness to take the AED to the incident scene.

In some embodiments, the visual alert includes a card/frame/pane/etc that includes a GUI widget such as an accept incident button that when selected, informs the server that someone has picked up the AED and has indicated that they are responding to the incident. The specific text or graphics associated with the accept incident button or other GUI widget may vary widely, but when the incident is accepted an Accept Incident message 727 is sent to the AED network server. By way of example, in some specific interfaces the AED user interface displays a button labeled, "I can help" or "Navigate to emergency" which when selected serve as acceptance of the incident. In other embodiments, the AED may be configured to understand spoken commands and the acceptance may be conveyed via a spoken response (e.g., a spoken "I can help"). Once the incident is accepted, the AED may display a map showing the location of the incident and/or provide directions to the incident as described in the incorporated patents mentioned above.

It should be appreciated that the set AEDs that are reported to the PSAP via the Resource List 720 may be quite different than the set of AED to which Nearby Incident messages 725 are sent. There are several reasons for this. In general, a goal of the Resource List is to provide the telecommunicator with an indication of accessible AED that a caller or bystander may go retrieve and bring to the scene of an incident. Thus, if an AED is in a restricted area that is not available to the public, it may not be desirable to show that AED on the dispatcher map (or if it is shown, it may be desirable to show it in a visually distinguishable manner with notes indicating its limited accessibility). An example of this may be an AED within a non-public location (e.g., a gated campus, a locked building, a personal residence, a vehicle, etc.). At the same time, when the owner/administrator has opted in, it may be desirable to send Nearby Incident Alerts to such devices since the individuals associated with the AED and/or bystanders may be very willing to bring that AED to treat a cardiac arrest victim. In another example, it may be desirable to send nearby incident alerts to AEDs that are further from the incident than might be reasonable to send a bystander to go fetch because it may be quite reasonable for a responder to bring that AED to the scene of the incident even if there are closer AEDs since 1 way travel of a responder with an AED in hand may be quicker than two-way travel of a bystander trying to locate an AED that they have never seen before.

From the foregoing, it should be apparent that it is often desirable for the set of AEDs that are pinged to check-in to be larger (sometimes much larger) that the set of AEDs that are expected to be eventually selected for inclusion in the set to be reported to the PSAP and/or to be sent Nearby Incident messages. As suggested above, one way to accomplish this is to send Check-in messages 710 to all AEDs expected to be within a larger distance of the incident than would be considered close to the incident.

Returning to FIG. 7, when a volunteer responder accepts an incident via an AED, an Accept Incident Message 727 is send from the corresponding AED 10 to the AED network server 20. The AED network server then sends a message to the PSAP indicating that the associated AED has accepted the incident, thereby providing feedback to the dispatcher that an AED is on the way (as represented by 728). In some embodiments, a separate "acceptance" message is sent to the PSAP. However, another approach is to include acceptance information in the Resource List. By way of example, this may be accomplished by providing a field in the Resource List that indicates whether the associated AED has "accepted" the incident. This can take the form of a simple "accepted incident" flag or any other suitable data structure. (Of course other flags/data structures may be included for each AED identified in the Resource List to convey other appropriate information about AEDs in the list, as for example a location field, a location/status confirmed flag, etc.).

When an AED has "accepted" an incident, the visual appearance of its corresponding icon on the display screen 404 may be changed or rendered differently relative to the icons 440 corresponding AEDs that have not accepted the incident so that the dispatcher can readily see which (if any) AEDs have accepted the incident and are being transported to the incident as represented by element 729. The nature of the visual distinction may vary widely in accordance with design preferences—by way of example, one or more of different colors, different sizes, different images, etc. may be used to differentiate accepting AEDs from others. FIG. 6B shows an example in which AED icons 441 corresponding to AEDs that have accepted the incident have a different visual appearance than the icons 440 corresponding to those AED that have not yet accepted the incident.

It should be apparent from the foregoing that there may be times when an "accepting" AED was not represented on the dispatcher map 406 prior to the AED's acceptance of an incident. In such cases, the location of the accepting AED would first be displayed for the telecommunicator to see after the acceptance. It should be appreciated that the Resource List framework described above works well for informing the PSAP of the previously unknown accepting AED because the new AED is simply added to the list.

In some embodiments, the AEDs are configured to send status messages and/or location updates to the AED network server on a regular basis after they have been used to accept an incident. In some specific implementations, the AED locations updates are sent as part of Status messages 730, with the AED's current location simply being a field in the status message. The frequency of the updates can vary widely. By way of example, update frequencies on the order of every 1 to 15 seconds will work well in many implementations. Of course longer or shorter intervals can be used as appropriate for any particular implementation. In this way, the AED network server is continually updated as to the accepting AED's current location. That updated location information is then conveyed to the dispatcher's workstation at the PSAP (e.g., via the Resource List or other suitable constructs), as represented by 732, which prompts the map to update the displayed location of the accepting AED, as represented by 733. In this way, the dispatcher can track the location of the accepting AED(s) in real time as they make their way to an incident and can convey any appropriate information/instructions to the caller based thereon. (e.g., "an AED should be arriving momentarily at your front door," "let them in" or "look for them.") An illustration of changes in the dispatcher's view as the AED moves towards the incident can be seen by comparing FIG. 6B to FIG. 6C, with the primary difference being that the illustrated location of the accepting AED(s) 441 have changed as they are carried towards the incident.

The AED status information (if any) beyond the AEDs location that is conveyed to the PSAP at 732 may vary widely based on the design goals. In some circumstances the full contents of the Status message 730 can be forwarded to the PSAP. However, in other embodiments that is not necessary and the status information provided to the PSAP is simply the location, and potentially ancillary or repeated information such as reiterating that the AED has accepted the incident and is in good working order.

The described connections also provide an effective communications path between that can be used to facilitate other communications between the accepting AED(s) or responders and the dispatcher. Some such communications may be freeform communications analogous to text messaging between the dispatcher and the user. Examples of that may be notes or other instructions entered by the dispatcher that are conveyed to the AED by way of the AED network server as represented by messages 735 and 736 or messages from the user to the dispatcher represented by messages 738 and 739. Other communications may be more structured. For example, in some embodiments, the AED may be configured to display an "I have arrived" message that the volunteer responder carrying the AED can select to inform the system that they have arrived at the scene of the incident. In one particular implementation, the AED displays an "I have arrived" button (or other suitable GUI) widget when it gets close to the location of the incident. Selection of the "I have arrived" button causes an Arrived message 741 to be transmitted from the AED to the AED network server 20, which can then forward the message to the PSAP as represented by Arrived message 742. When Arrived message 742 is received at the PSAP, a corresponding message is displayed on the dispatcher's display screen as represented by element 744, thereby affirmatively informing the dispatcher that the AED is now at the scene of the incident. In other embodiments, the Arrived message 741 and/or 742 may be triggered by other mechanisms, as for example by the AED being powered on or in response to a determination that the AEDs location is substantially the same as the location of the incident. Such determinations may be made by the AED itself, an interface unit associated with the AED, by the AED network server or by other suitable mechanisms.

The structure of the Resource List may vary widely based on the needs and design choices of a particular implementation. In some specific embodiments, the Resource List includes:

(1) a high-level status indicator, which may be one of the high-level responder network status indicator discussed above;

(2) a message timestamp;

(3) an array of relevant responder resources and information about such resources, in some embodiments, the information about each resource may include (i) a resource type identifier, which, by way of example may identify the resource as an AED, a volunteer responder, another type of device, etc.; (ii) a Resource Acceptance indicator (which may be a flag, a true/false indicator etc.) that indicates whether the resource has accepted the incident; (iii) a location field that provides the location of the resource (e.g., latitude, longitude, altitude and a confidence radius; GNSS coordinates, etc.); and optionally (iv) a resource descriptor which may provide relevant information about the resources—e.g., the AED is located next to the $3^{rd}$ floor elevator; Rob is trained in CPR; Mary is an off duty EMT, etc.

(4) a system identifier that identifies the AED responder network sending the message; and (5) a security key The user interface on the dispatcher terminal or portal can then utilize the conveyed information to render the appropriate information on the appropriate dispatcher's display screen.

It should be appreciated that the framework described above, which enables the dispatcher to (a) see the location of AEDs that are nearby an incident to facilitate directing bystanders to retrieve the AED in real time; (b) easily identify AEDs that are on their way to the incident; (c) see the progress of an AED as it is being carried to the incident; and optionally (d) communicate with a responder bringing an AED to an incident through that AED is a powerful tool that can enhance the dispatcher's ability to assist/guide bystanders and volunteer responders to provide emergency care to cardiac arrest victims prior to the arrival of professional EMS personnel.

Still further, as will be appreciated by those familiar with state of the art emergency response systems, some emergency response networks train their telecommunicators/dispatchers to actively encourage/direct bystanders to serve as caregivers that render aid to patients suffering from medical emergencies before emergency medical services (EMS) arrives. In the context of cardiac arrest, such efforts are frequently referred to as telephone/telecommunicator CPR (T-CPR). More specifically, when a telecommunicator, in partnership with the caller, identifies a patient suffering from cardiac arrest, the telecommunicator will provide AED use instructions and/or CPR instructions to the caller, as appropriate, in addition to quickly dispatching the appropriate EMS response. The belief is that the telecommunicator and the caller form a unique team in which the expertise of the telecommunicator and the willingness of the caller or a responder in proximity to the caller to provide CPR represents an opportunity to improve SCA survival rates. The American Heart Association provides T-CPR recommendations and guidance.

The Applicant has developed AEDs, systems and techniques that are well suited for enhancing T-CPR, some of which are described in U.S. Pat. No. 11,210,919 (P021), which is incorporated herein by reference. The AED/dispatcher communications path established as described above can also be used to transmit information about how the AED is being used during an incident, thereby facilitating T-CPR. In particular, the AED may send Status messages 750 to the AED network server after it has been activated for emergency use at the incident scene. The status messages 750 sent after the AED has been activated for emergency use may include information such as the current AED state or current AED instruction state and/or other information that may be useful to the dispatcher as described in the incorporated T-CPR patent. The AED network server may take appropriate information from the status messages and forward it to the PSAP for display on screen 404 to help give the telecommunicator a better understanding of what is happening at the incident scene, which can make it easier for the telecommunicator to give useful directions and encouragement to the caller.

In one specific example, the dispatcher UI on display screen 404 may include a field that identifies the current AED instruction state and a timer that indicates how long the AED has been in that state. From this information, the telecommunicator can follow where the responder user is in AED use flow and can determine if the user appears stuck on any particular step. For example, if the current AED instruction state is to place the defibrillation electrode pads on the patient's chest and there has been a delay in placing the pads or the pads have been placed incorrectly, the telecommunicator can provide the caller with specific instructions related to pad placement.

Of course, a wide variety of other AED information can be provided to the telecommunicator during the incident to further support T-CPR efforts as described in the incorporated T-CPR patent. By way of example, in some specific implementations, the dispatcher user interface may be configured to show one or more of: (i) an indication that the AED has been activated (or whether the AED has been activated); (ii) time since the AED was activated; (iii) whether the defibrillation electrode pads have been removed from the AED; (iv) whether the electrode pads have been placed on the victim; (v) how many shocks (if any) have been delivered (e.g., 0, 1, 2, etc); the most recent shockable/non-shockable victim heart rhythm analysis; and (vi) an Incident ID. Any or all of the foregoing can be relayed to EMS by the dispatcher (or by the AED network server).

In mentioned above, in some embodiments, the AED network server is configured to send nearby incident messages to volunteer responders and/or responder devices that are in the vicinity of an incident in addition to sending such messages to AEDs. The Nearby Incident message may be sent to the volunteer responders using any of a variety of different technologies. Often, volunteer responders will have an AED responder app on their cell phones or other mobile communications devices. Most modern cell phones have a notification service that can be used to push notifications to their users. For Apple devices incorporate the Apple Push Notification service (APNs) and Android devices include a Notifications service. Each of these services can be used to push a notification to a volunteer responder that will be displayed on the volunteer's device outside of the app's UI. The notification can be configured to either open the AED responder app, or take an action directly from the notification. For example, in some implementations, the message in the notification can be configured to allow the user to accept the incident directly from the notification by tapping on the notification or a specific button within the notification.

Although it is expected that volunteer responders would most typically be notified of nearby incidents via their cell phone, it should be appreciated that notifications can be delivered via a number of other pathways. For example many homes and offices have virtual assistant enabled smart speakers and the incident alerts can readily be delivered via the smart speakers. Additionally, there are a number of wearable devices that have communications capabilities including smart watches, smart glasses, fitness trackers and may other devices. In other embodiments, the AED network server can send nearby incident messages incident messages to any such devices. Some such systems are described in more detail in U.S. patent application Ser. No. 17/100,313 (P020B), which is incorporated herein by reference.

In general, accepting volunteer responders can be treated very similarly to accepting AEDs using the described frameworks regardless of the nature of the device that they use to communicate with the AED network server 20. In this way, the dispatcher can also see the location of volunteer responders that have indicated a willingness to help. The location(s) of the volunteer responders can be tracked and updated using substantially the same mechanisms described above with respect to the accepting AEDs so that the dispatcher can see the volunteer responders movement towards the incident. Preferably, only volunteer responders that have accepted the incident would be displayed to the dispatcher so that the dispatcher is not distracted by individuals that may not be available to help. However, in alternative embodiments, registered volunteer responders in the vicinity of the incident could be shown regardless of whether they have accepted the incident. Presumably accepting responders would be visually distinguishable from any non-accepting responders that are shown.

When desired, one or more fields associated with volunteer responders may include additional information about the responder that might be relevant to the telecommunicator. This can include situational information such as whether the volunteer responder has an AED in their possession, and/or personal information about the responder such as an indication of the volunteers is a doctor, an EMT or other trained responder.

In most of the embodiments described above, the Resource List is generalized to identify, and provide the location of all resources associated that deemed are relevant to the incident, including nearby AEDs, accepting AEDs, accepting volunteer responders or responder devices, etc. In other embodiments, separate Nearby AED Lists, Accepting AED Lists, Volunteer Responder/devices lists or notifications and/or combinations or sub-combinations thereof and or individual resource messages can be sent to the PSAP as desired for any particular implementation.

In some embodiments, when a volunteer responder that accepts an incident has an AED in their possession, their interactions with the AED network server (including actions such as tracking location and any desired messaging) may be handled through the AED responder App, the AED itself, or both.

Both the AED network server 20 and the dispatcher preferably have the ability to cancel the Nearby Incident Alerts when appropriate. There can be a wide variety of different triggers that will cause the network server to cancel a nearby incident alert. For example, the dispatcher user interface preferably has a mechanism (e.g., a GUI widget such as a cancel button) that can be selected to send a Cancel Alert message (not shown) to the AED network server. The AED network server, in turn, sends corresponding Cancel Alert messages to the AEDs that are generating nearby incident alerts or are on their way, but have not yet arrived at the incident scene. Such cancelation might be appropriate if/when the dispatcher learns that: (i) emergency medical personnel (e.g. an EMT, paramedic or ambulance) have arrived on the scene; (ii) other defibrillators have been brought to the scene; or (iii) the dispatcher has otherwise determined that an AED is not (or is no longer) needed.

Similarly, the AED network server itself may cancel the alert for any of a variety of reasons. For example, it may be desirable to cancel alerts generated by non-responding device after a designated number of AEDs and/or volunteers have indicated that they are responding to an incident. In another example, the alert may the cancelled by the AED network server (or the AED itself) based on a timeout criteria—e.g., that the AED has been generating an alert for too long without receiving a response.

In another example, a responding volunteer may indicate that they have arrived at the scene with an AED by selecting an appropriate GUI widget such as an "I've arrived" button on the AED display or on a volunteer responder's app. Once the AED network server has been informed that a defibrillator has arrived on the scene (or multiple defibrillators and/or volunteers have arrived on the scene if that is deemed preferable), the AED network server can send alert cancellation messages to the other alerted AEDs.

In another example, the AED may be configured to notify the AED server when it is deployed. In such circumstances, the AED network server can be configured to send alert cancelation messages to other AEDs once it learns that a responding AED has been activated or powered on for emergency use at the incident location. Such information can also be conveyed to the dispatcher so that the dispatcher is affirmatively aware that an AED is being deployed. Such "in use" notifications can be triggered by any of a variety of different actions, as for example based on any of (1) activating a "power on" button on the AED; (2) the withdrawal of the electrode pads from their storage location or the withdrawal of a pad cartridge from the AED; (3) attachment of the pads to a patient; (4) the detection of a cardiac rhythm, etc.

In the descriptions above, a number of communications between a PSAP and an AED response network server are described. It should be appreciated that such communications can be directly between those two system nodes, or they may pass through one or more intermediary such as the emergency services interface (ESI) described above with respect to FIG. 1B. Indeed, the ESI intermediary approach can be quite advantageous in many applications because some of the larger ESIs have already integrated with a large percentage of the PSAPs in the U.S. or in other jurisdiction. Therefore integrating through an ESI can be a simple and effective way to facilitate adoption in PSAPs that are already integrated with that PSAP. Similarly, the described system can be readily integrated with various computer aided dispatch (CAD) systems, which can provide another very effective way to integrate with PSAPs that utilize such those CAD systems. Therefore, when communications between a PSAP and an AED response network server are described, it should be understood that those communication may be direct, or take place via an ESI or other suitable intermediaries.

In the description above, a number of steps have been described or illustrated in a particular order. These include the transmission of the Check-in messages, status messages, resource lists, incident alerts, dispatcher notes, responders messages, arrived messages, etc. It should be appreciated that except where the context requires a specific order, the order in which these step occur may vary. For example, many of the communications are triggered by specific actions (e.g., actions of a dispatcher or volunteer responder), or in response to the receipt of new information,) and as such the actual timing of such actions may vary in accordance with the timing of their various triggers. Further, the relative timing at which the AED network server performs various tasks may vary based on the systems design in addition to specific triggers. For example, the timing of tasks such a sending an activation confirmation to the PSAP and sending check-in messages to AEDs (if any) are independent of one another. Similarly, the timing that informs the PSAP of nearby AEDs (e.g., by sending Resource Lists or via other appropriate mechanisms) relative to the timing of sending nearby incident messages to AEDs in its network are independent of one another. Similarly, the relative timing of alerting AEDs vs. responders or other devices may be independent of one another.

In many cases messages sent by the server will be based on the most current information then available to the server, and updates may be sent at designated intervals or as updated information is available. For example, due to factors such as network latency and device settings, there will sometimes be delays between the time a status query is sent and a responsive status report is received and it can be expected that the response times of different devices may vary—sometimes significantly. Thus, when desired, the selection of devices to inform the PSAP of and/or to send a nearby incident message to can be based on the information then available to the AED network server and may be updated by sending updated messages to the PSAP or sending additional nearby incident messages as appropriate as new information is received.

Further when desired, some of the described steps can be eliminated entirely or in part. For example, certain AEDs known or believed to be within a certain range of the incident based on pre-existing information may be sent a nearby incident message and/or included in a Resource List immediately upon the receipt of an activate AED responder network request regardless of whether the location and/or status of other nearby AEDs is checked prior to including them in the list presented to the dispatcher or in the emergency response.

In some of the described embodiments the PSAP dispatcher is able to enter notes to be presented to potential responders. Such notes can be entered by the dispatcher and/or presented to potential responders at any appropriate time. For example, notes may be entered before the Activate AED Responder Network message is sent. In such circumstances the notes may be included with the initial responder network activation request sent from the PSAP to the responder network server. The server, in turn may pass the notes to contacted responders and AEDs. When desired, the notes can be forwarded as part of the Nearby Incident Message 725 (i.e., when the AED is first informed of a nearby incident) or after the AED or responder has accepted an incident. In some implementations, notes that accompany the Nearby Incident Message 725 may be displayed as part of the Nearby Incident Alert generated by the AED. In other embodiments, the notes may be initially displayed after a potential responder has "accepted" the incident or at any other time deemed appropriate by the system designer. It should be apparent that messages conveyed by way of the notes can potentially be helpful both in terms of encouraging bystanders to actually respond to an incident, and in conveying information that can make their response quicker or more efficient.

In some embodiments, dispatchers can enter notes at any time—as for example, after an incident has been accepted, as more information becomes available, etc. The notes are then forwarded as appropriate. For example, the later messages may be sent only to accepting AEDs and/or accepting volunteer responders as desired. The ability to send messages to responding AEDs can be a very helpful tool that the dispatcher can use to motivate and assist bystanders and others willing to respond to a nearby cardiac arrest incident even before they have reached the incident or activated the AED for emergency use. When desired, such messaging can continue even after the AED has arrived at, or has been deployed at, the incident location.

Although only a few embodiments of the invention have been described in detail, it should be appreciated that the invention may be implemented in many other forms without departing from the spirit or scope of the invention. Therefore, the present embodiments should be considered illustrative and not restrictive and the invention is not to be limited to the details given herein, but may be modified within the scope and equivalents of the appended claims.

What is claimed is:

1. A dispatcher user interface suitable for display on a display screen at a public-safety answering point (PSAP), the dispatcher user interface configured to:
   provide a GUI widget that a dispatcher can utilize to activate a responder network that includes one or more automated external defibrillators (AEDs) of an emergency incident;
   display an accepting AED icon on a map that includes a location of the emergency incident, the accepting AED icon being indicative of a location of a first AED that has been used to accept the emergency incident; and
   periodically update the placement of the accepting AED icon on the map to show an updated location of the first AED, whereby the dispatcher may see an estimation of a then current location of the first AED as the first AED is transported to the location of the emergency incident.

2. A dispatcher user interface as recited in claim 1 further configured to display one or more nearby AED icons on the map, each nearby AED icon showing a location of a corresponding AED whose location and operational status have been confirmed in real time relative to the emergency incident, wherein the nearby AED icons have a different visual appearance than the accepting AED icon.

3. A dispatcher user interface as recited in claim 2 further configured to display a set of one or more volunteer responder icons on the map, each volunteer responder icon indicative of a location of a volunteer responder that has accepted the emergency incident, wherein the volunteer icons have a different visual appearance than the accepting AED icons and the nearby AED icons, and wherein locations of volunteer responders that have not accepted the emergency incident are not displayed on the map.

4. A dispatcher user interface as recited in claim 1 further comprising:
a first GUI widget suitable for receiving an input from the dispatcher that at least one of inputs, selects or confirms the location of the emergency incident;
a second GUI widget that when activated by the dispatcher causes a responder network activation message to be sent that directly or indirectly causes one or more AEDs that are in a vicinity of the emergency incident to generate a nearby incident alert configured to inform bystanders that there is a potential medical incident nearby for which the AED may be helpful.

5. A dispatcher user interface as recited in claim 1 further comprising:
a first GUI widget suitable for receiving dispatcher notes input by the dispatcher; and
a second GUI widget that when activated by the dispatcher causes a responder network activation message to be sent that directly or indirectly causes one or more AEDs that are in a vicinity of the emergency incident to generate a nearby incident alert configured to inform bystanders that there is a potential medical incident nearby for which the AED may be helpful, wherein when the dispatcher notes are present at the time the network activation message is sent, the dispatcher notes are transmitted as part of or together with the network activation message.

6. A dispatcher user interface as recited in claim 1 further configured to alter the appearance of the accepting AED icon when the first AED arrives at the location of the emergency incident.

7. A dispatcher user interface as recited in claim 6 wherein the appearance of the accepting AED icon is altered in response to an arrived message transmitted by the associated AED to the dispatcher user interface in response to an arrived input made by a responder on the associated AED.

8. A dispatcher user interface as recited in claim 1 wherein the first AED is deemed to have accepted the emergency when the dispatcher user interface receives a notification that a responder has made an acceptance input to the first AED.

9. A dispatcher user interface as recited in claim 1 further configured to:
display multiple accepting AED icon on the map when multiple AEDs are used to accept the emergency incident, each accepting AED icon being indicative of a location of an associated AED that has accepted the emergency incident; and
periodically update the placement of each accepting AED icon on the map to show an updated location of the associated AEDs as the associated AEDs are transported to the location of the emergency incident, whereby the dispatcher may see estimations of then current locations of the associated AEDs as the associated AEDs are transported to the location of the emergency incident.

10. A dispatcher user interface as recited in claim 1 wherein the location of the accepting AED icon is updated at least once every fifteen (15) seconds while the first AED is being transported to the location of the emergency incident.

11. A dispatcher user interface as recited in claim 1 further comprising mechanisms configured for:
at least one of inputting, selecting or confirming a location of an emergency incident; and
inputting dispatcher notes; and
wherein the GUI widget is configured for causing a responder network activation message to be sent that directly or indirectly causes one or more of the AEDs that are in a vicinity of the emergency incident to generate a nearby incident alert configured to inform bystanders that there is a potential medical incident nearby for which the AED may be helpful.

12. A dispatcher user interface as recited in claim 11 wherein the responder network activation message includes geographic coordinates of the location of the emergency incident.

13. A dispatcher user interface as recited in claim 11 wherein the responder network activation message includes the dispatcher notes inputted by a dispatcher.

14. A dispatcher user interface as recited in claim 11 wherein the responder network activation message is sent directly or indirectly to a responder network server that selects the one or more of the AEDs and sends nearby incident messages to the one or more of the AEDs thereby causing each of the one or more of the AEDs to generate the nearby incident alert.

15. A dispatcher user interface suitable for display on a dispatcher display screen at a public-safety answering point (PSAP), the dispatcher user interface configured to:
display a first set of one or more first icons on a map that shows the location of an emergency incident, each first icon indicative of a location of a corresponding AED that is nearby the emergency incident;
display a second set of one or more second icons on the map, each second icon indicative of a location of a corresponding AED that has accepted the emergency incident; and
wherein the first and second icons have different visual appearances.

16. A dispatcher user interface as recited in claim 15, wherein an AED is deemed to have accepted the emergency when a responder makes an acceptance input to the corresponding AED.

17. A dispatcher user interface as recited in claim 15 further configured to periodically update the placement of each second icon to show an updated current location of the corresponding AED as the corresponding AED is transported to the location of the emergency incident.

18. A dispatcher user interface as recited in claim 15 wherein the locations of the AEDs represented by the first and second icons are obtained from such AEDs in real time during the emergency incident.

19. A dispatcher user interface as recited in claim 15 further configured to display a third set of one or more third icons on the map, each third icon indicative of a location of a volunteer responder that has accepted the emergency incident, wherein the third icons have a different visual appearance than the first and second icons.

20. A dispatcher user interface as recited in claim 19 wherein locations of volunteer responders that have not accepted the emergency incident are not displayed on the map.

21. A dispatcher user interface as recited in claim 19 wherein the third icons have a different visual appearance than the first and second icons.

22. A dispatcher user interface as recited in claim 19 wherein at least some of the volunteer responders are notified of the incident by way of at least one selected from the group consisting of:
- a smart speaker;
- a security system; and
- a wearable device.

23. A dispatcher user interface as recited in claim 15 configured such that each AED in the first set is constrained to within a first designated distance or a first estimated response time of the emergency incident and AED(s) in the second set are not constrained to be within the first designated distance or the first estimated response time.

24. A dispatcher user interface as recited in claim 15 wherein the different visual appearance is or includes at least one of a different color, a different size and a different shape.

* * * * *